US012637676B2

(12) United States Patent
Grainok et al.

(10) Patent No.: US 12,637,676 B2
(45) Date of Patent: May 26, 2026

(54) TREATMENT OF OPTIC ATROPHY

(71) Applicant: PYC Therapeutics Limited, Perth (AU)

(72) Inventors: Janya Grainok, Perth (AU); Ianthe Pitout, Perth (AU); Sasiwimon Utama, Perth (AU); Kim Rice, Melbourne (AU)

(73) Assignee: PYC Therapeutics Limited, Perth (AU)

( * ) Notice: Subject to any disclaimer, the term of this patent is extended or adjusted under 35 U.S.C. 154(b) by 556 days.

(21) Appl. No.: 18/026,388

(22) PCT Filed: Oct. 1, 2021

(86) PCT No.: PCT/AU2021/051154
§ 371 (c)(1),
(2) Date: Mar. 15, 2023

(87) PCT Pub. No.: WO2022/067398
PCT Pub. Date: Apr. 7, 2022

(65) Prior Publication Data
US 2023/0407310 A1        Dec. 21, 2023

(30) Foreign Application Priority Data

Oct. 2, 2020    (AU) ................................ 2020903577

(51) Int. Cl.
*C12N 15/113*        (2010.01)
*A61P 27/02*        (2006.01)

(52) U.S. Cl.
CPC .......... *C12N 15/1137* (2013.01); *A61P 27/02* (2018.01); *C12Y 306/05005* (2013.01); *C12N 2310/11* (2013.01); *C12N 2310/314* (2013.01); *C12N 2310/321* (2013.01); *C12N 2310/3233* (2013.01); *C12N 2310/3513* (2013.01); *C12N 2320/33* (2013.01)

(58) Field of Classification Search
CPC ............ C12N 15/1137; C12N 2310/11; C12N 2310/314; C12N 2310/321; C12N 2310/3525; C12N 2320/33; A61K 31/7088
See application file for complete search history.

(56) References Cited

FOREIGN PATENT DOCUMENTS

| | | |
|---|---|---|
| RU | 2008859 C1 | 3/1994 |
| WO | 2010/091878 A2 | 8/2010 |
| WO | 2019/084050 A1 | 5/2019 |
| WO | 2021/231107 A1 | 11/2021 |

OTHER PUBLICATIONS

See Venkatesh et al. (Nucleic Acid Therapeutics vol. 34, No. 5, 2024).*

(Continued)

*Primary Examiner* — Terra C Gibbs

(74) *Attorney, Agent, or Firm* — McCarter & English, LLP; Marcie B. Clarke; Samantha E.R. Dundon

(57) ABSTRACT

An isolated or purified antisense oligomer for modulating mRNA translation of the OPA1 gene transcript or part thereof which has a modified backbone structure and sequences with at least 75% sequence identity to the isolated or purified antisense oligomer.

11 Claims, 12 Drawing Sheets

Specification includes a Sequence Listing.

SEQ ID NO: 61

(56) References Cited

OTHER PUBLICATIONS

Gene Vision, downloaded from Dominant Optic Atrophy: for patients—Gene Vision on Sep. 8, 2025.*

Bonifert et al., Antisense Oligonucleotide Mediated Splice Correction of a Deep Intronic Mutation in OPA1. Mol Ther Nucleic Acids. Nov. 22, 2016;5(11):8 pages.

Liang et al., Translation efficiency of mRNAs is increased by antisense oligonucleotides targeting upstream open reading frames. Nat Biotechnol. Aug. 2016;34(8):875-80.

Venkatesh et al., Antisense oligonucleotide mediatedincrease of OPA1 expression using TANGOtechnology for the treatment of autosomal dominant optic atrophy. Investigative Ophthalmology & Visual Science. Jun. 2020;61, 2 pages.

Xiao et al., Exploration of AON-based uORF Blockage to Counteract OPA1 Haploinsufficiency. Young Researcher Vision Camp—An International Career Building Symposium. Jul. 12-14, 2019;one page.

Xiao, Ting, Institute for Opthalmic Research, Wissinger Lab, University ofTubingen. Oct. 22, 2019;3 pages.

International Search Report and Written Opinion for Application No. PCT/AU2021/0511543, dated Dec. 14, 2021, 14 pages.

Ausma, New drug for substantial unmet need added to PYC's pipeline. PYC Therapeutics, ASX Announcement. 4 pages, Oct. 12, 2020.

Chai et al., PYC-001, a peptide-conjugated phosphorodiamidate morpholino oligomer for the treatment of autosomal dominant optic atrophy. PYC Therapeutics. 1 page. (2023).

Das et al., PYC-001, a peptide-conjugated phosphorodiamidate morpholino oligomer for the treatment of autosomal dominant optic atrophy. PYC Therapeutics. Poster Presentation. 1 page, (2023).

Das et al., PYC-001, a peptide-conjugated phosphorodiamidate morpholino oligomer for the treatment of autosomal dominant optic atrophy. PYC Therapeutics. Poster Presentation. 1 page, (2023). version 2.

Grainok et al., PYC-001, a Peptide Conjugated Oligonucleotide for the Treatment of Autosomal Dominant Optic Atrophy. PYC Therapeutics. 1 page (2024).

Grainok et al., PYC-001, a Peptide Conjugated Oligonucleotide for the Treatment of Autosomal Dominant Optic Atrophy. PYC Therapeutics. 1 page (2024). Version 2.

Grainok et al., PYC-001: A Promising RNA Therapeutic for Autosomal Dominant Optic Atrophy. ARVO Annual Meeting Abstract. Investigative Ophthalmology & Visual Science. Jun. 2024;65:Abstract 5305, 2 pages.

Herkenne et al., Developmental and Tumor Angiogenesis Requires the Mitochondria-Shaping Protein Opa1. Cell Metab. May 5, 2020;31(5):987-1003.

Herkenne et al., OPA1, a new mitochondrial target in cancer therapy. Aging (Albany NY). Nov. 13, 2020;12(21):20931-20933.

Karaki et al., Antisense Oligonucleotides, A Novel Developing Targeting Therapy. Antisense Therapy. IntechOpen. 19 pages, (2019).

Mudumba et al., PYC-001, a Peptide Conjugated Oligonucleotide for the Treatment of Autosomal Dominant Optic Atrophy. NANOS Abstract. 1 page, (2024).

Ong et al., PYC-001, a Peptide Conjugated Oligonucleotide for the Treatment of Autosomal Dominant Optic Atrophy. PYC Therapeutics. 1 page (2024).

Ong et al., PYC-001: A Promising RNA Therapeutic for Autosomal Dominant Optic Atrophy. TIDES. 1 page, (2024).

PYC Therapeutics, FDA Grants Rare Pediatric Disease Designation to PYC Drug Development Program. Press Release. 3 pages, Aug. 30, 2024.

PYC Therapeutics, First ADOA Patient Dosed in Clinical Trial. Press Release. 4 pages, Nov. 1, 2024.

PYC Therapeutics, GLP TOX Results Clear Path for Second Blinding Eye Disease Drug to Enter Human Trials. Press Release. 5 pages, May 14, 2024.

PYC Therapeutics, Life-changing science. Investor update on ADOA drug program. Slideshow. 17 pages, Oct. 5, 2023.

PYC Therapeutics, PYC and FDA Align on Clinical Trial Pathway in ADOA. Press Release. 3 pages, Nov. 6, 2023.

PYC Therapeutics, PYC Announces Second Drug Program With Efficacy Data in Patient Cell Models. Press Release. 4 pages, May 18, 2021.

PYC Therapeutics, PYC Therapeutics Set To Announce Efficacy Results For Second Investigational Drug Program. Press Release, 3 pages, May 3, 2021.

PYC Therapeutics, PYC to Start Human Trials in Second Blinding Eye Disease. Press Release. 4 pages, Aug. 15, 2024.

PYC Therapeutics, PYC's VP-002 program for Autosomal dominant optic atrophy. slideshow. 18 pages, Jun. 2021.

PYC Therapeutics, Second Drug Program Effective in Both Non-human Primates and Patient-derived Models. Press Release. 6 pages, Oct. 4, 2023.

PYC Therapeutics, Second Drug Program Progressing Towards Human Trials. Press Release. 6 pages, Jun. 8, 2021.

PYC Therapeutics, US FDA Grants Orphan Drug Designation to PYC Drug Candidate. Press Release. 3 pages, May 24, 2024.

* cited by examiner

```
                    SEQUENCE LISTING

<160> NUMBER OF SEQ ID NOS: 60

<210> SEQ ID NO 1
<211> LENGTH: 23
<212> TYPE: DNA
<213> ORGANISM: Homo sapiens

<400> SEQUENCE: 1
accagcgcat gcgcacagtg cgt                                    23

<210> SEQ ID NO 2
<211> LENGTH: 22
<212> TYPE: DNA
<213> ORGANISM: Homo sapiens

<400> SEQUENCE: 2
aggaccagcg catgcgcaca gt                                     22

<210> SEQ ID NO 3
<211> LENGTH: 21
<212> TYPE: DNA
<213> ORGANISM: Homo sapiens

<400> SEQUENCE: 3
gtccgctgag gaccagcgca t                                      21

<210> SEQ ID NO 4
<211> LENGTH: 21
<212> TYPE: DNA
<213> ORGANISM: Homo sapiens

<400> SEQUENCE: 4
tttctaggcg ggcagcacga a                                      21

<210> SEQ ID NO 5
<211> LENGTH: 23
<212> TYPE: DNA
<213> ORGANISM: Homo sapiens

<400> SEQUENCE: 5
caaccacttc accctttcta ggc                                    23

<210> SEQ ID NO 6
<211> LENGTH: 19
<212> TYPE: DNA
<213> ORGANISM: Homo sapiens

<400> SEQUENCE: 6
aaccacttca ccctttcta                                         19
```

```
<210> SEQ ID NO 7
<211> LENGTH: 25
<212> TYPE: DNA
<213> ORGANISM: Homo sapiens

<400> SEQUENCE: 7
acccgtactc agtccgtcac ggaaa                                          25

<210> SEQ ID NO 8
<211> LENGTH: 22
<212> TYPE: DNA
<213> ORGANISM: Homo sapiens

<400> SEQUENCE: 8
cgtactcagt ccgtcacgga aa                                             22

<210> SEQ ID NO 9
<211> LENGTH: 25
<212> TYPE: DNA
<213> ORGANISM: Homo sapiens

<400> SEQUENCE: 9
acttccgcaa gagcctgaca ggcac                                          25

<210> SEQ ID NO 10
<211> LENGTH: 20
<212> TYPE: DNA
<213> ORGANISM: Homo sapiens

<400> SEQUENCE: 10
ggacttccgc aagagcctga                                                20

<210> SEQ ID NO 11
<211> LENGTH: 25
<212> TYPE: DNA
<213> ORGANISM: Homo sapiens

<400> SEQUENCE: 11
caatggcgca tggacttccg caaga                                          25

<210> SEQ ID NO 12
<211> LENGTH: 20
<212> TYPE: DNA
<213> ORGANISM: Homo sapiens

<400> SEQUENCE: 12
ctcccaatgg cgcatggact                                                20

<210> SEQ ID NO 13
<211> LENGTH: 19
<212> TYPE: DNA
<213> ORGANISM: Homo sapiens

<400> SEQUENCE: 13
cccaggaagt ggtcctcag                                                 19

<210> SEQ ID NO 14
<211> LENGTH: 19
<212> TYPE: DNA
<213> ORGANISM: Homo sapiens

<400> SEQUENCE: 14
```

-continued

```
ggctcccggt ccaggaatg                                          19

<210> SEQ ID NO 15
<211> LENGTH: 19
<212> TYPE: DNA
<213> ORGANISM: Homo sapiens

<400> SEQUENCE: 15
tcacgcaggt gctgagacg                                          19

<210> SEQ ID NO 16
<211> LENGTH: 22
<212> TYPE: DNA
<213> ORGANISM: Homo sapiens

<400> SEQUENCE: 16
cgtggaggac cagtgcatgc gc                                      22

<210> SEQ ID NO 17
<211> LENGTH: 21
<212> TYPE: DNA
<213> ORGANISM: Homo sapiens

<400> SEQUENCE: 17
aacggtccgc ggaggaccag c                                       21

<210> SEQ ID NO 18
<211> LENGTH: 22
<212> TYPE: DNA
<213> ORGANISM: Homo sapiens

<400> SEQUENCE: 18
gcacgaacgg tccgcggagg ac                                      22

<210> SEQ ID NO 19
<211> LENGTH: 22
<212> TYPE: DNA
<213> ORGANISM: Homo sapiens

<400> SEQUENCE: 19
ggcagtacga acggtctgcg ga                                      22

<210> SEQ ID NO 20
<211> LENGTH: 22
<212> TYPE: DNA
<213> ORGANISM: Homo sapiens

<400> SEQUENCE: 20
ggtgggcagc acgaatggtc cg                                      22

<210> SEQ ID NO 21
<211> LENGTH: 22
<212> TYPE: DNA
<213> ORGANISM: Homo sapiens

<400> SEQUENCE: 21
tctaggcggg cagcacgaac gg                                      22

<210> SEQ ID NO 22
<211> LENGTH: 22
<212> TYPE: DNA
<213> ORGANISM: Homo sapiens

<400> SEQUENCE: 22
```

-continued cctttctagg cgggcagcac ga                                              22

<210> SEQ ID NO 23
<211> LENGTH: 22
<212> TYPE: DNA
<213> ORGANISM: Homo sapiens

<400> SEQUENCE: 23
tcaccctttc taggcgggca gc                                              22

<210> SEQ ID NO 24
<211> LENGTH: 25
<212> TYPE: DNA
<213> ORGANISM: Homo sapiens

<400> SEQUENCE: 24
aaccacttca ccctttctag gcggg                                           25

<210> SEQ ID NO 25
<211> LENGTH: 25
<212> TYPE: DNA
<213> ORGANISM: Homo sapiens

<400> SEQUENCE: 25
gaaacaacca cttcaccctt tctag                                           25

<210> SEQ ID NO 26
<211> LENGTH: 25
<212> TYPE: DNA
<213> ORGANISM: Homo sapiens

<400> SEQUENCE: 26
tcacggaaac aaccacttca ccctt                                           25

<210> SEQ ID NO 27
<211> LENGTH: 25
<212> TYPE: DNA
<213> ORGANISM: Homo sapiens

<400> SEQUENCE: 27
gtccgtcacg gaaacaacca cttca                                           25

<210> SEQ ID NO 28
<211> LENGTH: 25
<212> TYPE: DNA
<213> ORGANISM: Homo sapiens

<400> SEQUENCE: 28
actcagtccg tcacggaaac aacca                                           25

<210> SEQ ID NO 29
<211> LENGTH: 25
<212> TYPE: DNA
<213> ORGANISM: Homo sapiens

<400> SEQUENCE: 29
caggcacccg tactcagtcc gtcac                                           25

<210> SEQ ID NO 30
<211> LENGTH: 25
<212> TYPE: DNA
<213> ORGANISM: Homo sapiens -continued

```
<400> SEQUENCE: 30
cctgacaggc acccgtactc agtcc                                          25

<210> SEQ ID NO 31
<211> LENGTH: 23
<212> TYPE: DNA
<213> ORGANISM: Homo sapiens

<400> SEQUENCE: 31
gagcctgaca ggcacccgta ctc                                            23

<210> SEQ ID NO 32
<211> LENGTH: 22
<212> TYPE: DNA
<213> ORGANISM: Homo sapiens

<400> SEQUENCE: 32
gcaagagcct gacaggcacc cg                                             22

<210> SEQ ID NO 33
<211> LENGTH: 22
<212> TYPE: DNA
<213> ORGANISM: Homo sapiens

<400> SEQUENCE: 33
aagtggccct cagcagcaag gg                                             22

<210> SEQ ID NO 34
<211> LENGTH: 24
<212> TYPE: DNA
<213> ORGANISM: Homo sapiens

<400> SEQUENCE: 34
acctaggaag tggtcctcag cagc                                           24

<210> SEQ ID NO 35
<211> LENGTH: 25
<212> TYPE: DNA
<213> ORGANISM: Homo sapiens

<400> SEQUENCE: 35
ggaatgaccc aggaagtggc cctca                                          25

<210> SEQ ID NO 36
<211> LENGTH: 25
<212> TYPE: DNA
<213> ORGANISM: Homo sapiens

<400> SEQUENCE: 36
gtccaggaat gacccaggaa gtggc                                          25

<210> SEQ ID NO 37
<211> LENGTH: 25
<212> TYPE: DNA
<213> ORGANISM: Homo sapiens

<400> SEQUENCE: 37
ctgacaggca cccgtactca gtccg                                          25

<210> SEQ ID NO 38
<211> LENGTH: 25
<212> TYPE: DNA
<213> ORGANISM: Homo sapiens
```

-continued

<400> SEQUENCE: 38
gcctgacagg cacccgtact cagtc                                            25

<210> SEQ ID NO 39
<211> LENGTH: 25
<212> TYPE: DNA
<213> ORGANISM: Homo sapiens

<400> SEQUENCE: 39
agcctgacag gcacccgtac tcagt                                            25

<210> SEQ ID NO 40
<211> LENGTH: 25
<212> TYPE: DNA
<213> ORGANISM: Homo sapiens

<400> SEQUENCE: 40
gagcctgaca ggcacccgta ctcag                                            25

<210> SEQ ID NO 41
<211> LENGTH: 25
<212> TYPE: DNA
<213> ORGANISM: Homo sapiens

<400> SEQUENCE: 41
agagcctgac aggcacccgt actca                                            25

<210> SEQ ID NO 42
<211> LENGTH: 25
<212> TYPE: DNA
<213> ORGANISM: Homo sapiens

<400> SEQUENCE: 42
aagagcctga caggcacccg tactc                                            25

<210> SEQ ID NO 43
<211> LENGTH: 25
<212> TYPE: DNA
<213> ORGANISM: Homo sapiens

<400> SEQUENCE: 43
caagagcctg acaggcaccc gtact                                            25

<210> SEQ ID NO 44
<211> LENGTH: 25
<212> TYPE: DNA
<213> ORGANISM: Homo sapiens

<400> SEQUENCE: 44
gcaagagcct gacaggcacc cgtac                                            25

<210> SEQ ID NO 45
<211> LENGTH: 25
<212> TYPE: DNA
<213> ORGANISM: Homo sapiens

<400> SEQUENCE: 45
ctgacaggca ttcgtactca gtccg                                            25

<210> SEQ ID NO 46
<211> LENGTH: 25
<212> TYPE: DNA

-continued

```
<213> ORGANISM: Homo sapiens

<400> SEQUENCE: 46
gcctgacagg cacttgtact cagtc                                          25

<210> SEQ ID NO 47
<211> LENGTH: 25
<212> TYPE: DNA
<213> ORGANISM: Homo sapiens

<400> SEQUENCE: 47
agcctgacag gcattcgtac tcagt                                          25

<210> SEQ ID NO 48
<211> LENGTH: 25
<212> TYPE: DNA
<213> ORGANISM: Homo sapiens

<400> SEQUENCE: 48
gagcttgaca ggcacctgta ctcag                                          25

<210> SEQ ID NO 49
<211> LENGTH: 25
<212> TYPE: DNA
<213> ORGANISM: Homo sapiens

<400> SEQUENCE: 49
agagcttgac aggcactcgt actca                                          25

<210> SEQ ID NO 50
<211> LENGTH: 25
<212> TYPE: DNA
<213> ORGANISM: Homo sapiens

<400> SEQUENCE: 50
aagagcttga caggcactcg tactc                                          25

<210> SEQ ID NO 51
<211> LENGTH: 25
<212> TYPE: DNA
<213> ORGANISM: Homo sapiens

<400> SEQUENCE: 51
caagagcttg acaggcatcc gtact                                          25

<210> SEQ ID NO 52
<211> LENGTH: 25
<212> TYPE: DNA
<213> ORGANISM: Homo sapiens

<400> SEQUENCE: 52
gcaagagctt gacaggcatc cgtac                                          25

<210> SEQ ID NO 53
<211> LENGTH: 25
<212> TYPE: DNA
<213> ORGANISM: Homo sapiens

<400> SEQUENCE: 53
aacaaccact tcaccctttc taggc                                          25

<210> SEQ ID NO 54
<211> LENGTH: 24
```

```
<212> TYPE: DNA
<213> ORGANISM: Homo sapiens

<400> SEQUENCE: 54
acaaccactt caccctttct aggc                                                24

<210> SEQ ID NO 55
<211> LENGTH: 25
<212> TYPE: DNA
<213> ORGANISM: Homo sapiens

<400> SEQUENCE: 55
acaaccactt caccctttct aggcg                                               25

<210> SEQ ID NO 56
<211> LENGTH: 25
<212> TYPE: DNA
<213> ORGANISM: Homo sapiens

<400> SEQUENCE: 56
aaacaaccac ttcacccttt ctagg                                               25

<210> SEQ ID NO 57
<211> LENGTH: 23
<212> TYPE: DNA
<213> ORGANISM: Homo sapiens

<400> SEQUENCE: 57
caaccacttt accctttcta ggc                                                 23

<210> SEQ ID NO 58
<211> LENGTH: 23
<212> TYPE: DNA
<213> ORGANISM: Homo sapiens

<400> SEQUENCE: 58
caaccacttc atcctttcta ggc                                                 23

<210> SEQ ID NO 59
<211> LENGTH: 18
<212> TYPE: DNA
<213> ORGANISM: Homo sapiens

<400> SEQUENCE: 59
acttccgcaa gagcctga                                                       18

<210> SEQ ID NO 60
<211> LENGTH: 18
<212> TYPE: DNA
<213> ORGANISM: Homo sapiens

<400> SEQUENCE: 60
tcccaatggc gcatggac                                                       18
```

TREATMENT OF OPTIC ATROPHY

RELATED APPLICATIONS

This application is a 35 U.S.C. § 371 national stage filing of International Application No. PCT/AU2021/051154, filed on Oct. 1, 2021, which claims priority to Australian Application No. 2020903577, filed on Oct. 2, 2020. The contents of each of the aforementioned applications are hereby incorporated by reference in their entireties.

TECHNICAL FIELD

The present invention relates to the use of antisense oligomers to treat, prevent or ameliorate the effects caused by mutations in the gene OPA1.

BACKGROUND ART

Autosomal dominant optic atrophy (ADOA) is the world's commonest hereditary optic neuropathy, with an estimated disease prevalence ranging from 1 in 10,000 to 1 in 50,000. OPA1 is the major causative gene in most families with ADOA.

ADOA classically presents in early childhood with progressive visual failure, with selective retinal ganglion cell loss as its defining pathological characteristic. The mean age of onset of visual failure is 7 years, with a range of 1 to 16 years. 80% of affected individuals are symptomatic before the age of 10 years. In up to 20% of cases, ADOA has been associated with other clinical manifestations, most commonly sensorineural deafness, ataxia, myopathy and progressive external ophthalmoplegia. The significance of these syndromal ADOA variants has been highlighted by the identification of cytochrome c oxidase (COX)-deficient muscle fibres and multiple mtDNA deletions in skeletal muscle biopsies from these patients, implicating a role of OPA1 in mitochondrial DNA maintenance.

OPA1 consists of 30 exons spanning 100 kb of genomic DNA on the long arm of chromosome 3 (3q28-q29), and the protein product is a 960 amino acid polypeptide which co-localizes to the inner mitochondrial membrane. OPA1 contains a highly conserved functional GTPase domain shared by members of the dynamin superfamily of mechanoenzymes and regulates several important cellular processes including the stability of the mitochondrial network. Over 400 different OPA1 mutations have been reported responsible for optic nerve degeneration and visual loss, ranging from isolated 'Dominant Optic Atrophy' (DOA; OMIM #165500) to more severe multi-systemic syndromes named 'DOAplus' (OMIM #125250), including some bi-allelic cases with Behr Syndrome (OMIM #210000).

OPA1 is a ubiquitously expressed mitochondrial GTPase that is indispensable for mitochondrial function. In humans, OPA1 generates at least eight variants via differential splicing of exons 4, 4b and 5b. OPA1 precursor proteins are targeted and mobilised to the mitochondria by their mitochondrial targeting sequence (MTS). In the mitochondria, the OPA1 precursor proteins are cleaved into either long forms (I forms) which are anchored to the inner mitochondrial membrane, or into short, soluble forms (s forms).

The coding sequence of the full OPA1 gene is beyond the capacity of AAV vectors which have a limit of less than 5 kb. Furthermore, CRISPR/Cas9 gene correction will require a different product for each family's OPA1 mutation. In addition, both the gene replacement and gene editing approaches require subretinal injection of viral vectors to achieve adequate transfection. This carries risks of retinal trauma.

There is a need to provide new treatments or preventative measures for ADOA, or at least the provision of methods to compliment the previously known treatments. The present invention seeks to provide an improved or alternative method for treating, preventing or ameliorating the effects of ADOA.

The previous discussion of the background art is intended to facilitate an understanding of the present invention only. The discussion is not an acknowledgement or admission that any of the material referred to is or was part of the common general knowledge as at the priority date of the application.

SUMMARY OF INVENTION

The invention provides a means to increase levels of functional OPA1 protein expression. Preferably the increased functional OPA1 is in patients who have ADOA, more preferably in ADOA where OPA1 haploinsufficiency is implicated.

Broadly, according to one aspect of the invention, there is provided an isolated or purified antisense oligomer that targets the 5'UTR of the OPA1 gene transcript. Preferably there is provided an isolated or purified antisense oligomer to increase translation of functional OPA1 protein through steric inhibition of 5'UTR secondary structure elements and/or inhibition of upstream open reading frames. Preferably, there is provided an isolated or purified antisense oligomer for inducing increased production of the OPA1 protein or part thereof.

In one aspect of the invention, there is provided an antisense oligomer of 10 to 50 nucleotides comprising a targeting sequence complementary to a region near or within the 5'UTR of the OPA1 gene transcript or part thereof. In another aspect of the invention, there is provided an antisense oligomer of 10 to 50 nucleotides comprising a targeting sequence complementary to a region near or within an exon of the OPA1 gene transcript or part thereof.

According to an aspect of the invention, there is provided an isolated or purified antisense oligomer designed to increase translation of functional OPA1 protein through steric inhibition of 5'UTR secondary structure elements. Preferably, the antisense oligomer is a phosphorodiamidate morpholino oligomer.

Preferably, the antisense oligomer is selected from the group comprising the sequences set forth in Table 1 and combinations or cocktails thereof.

More specifically, the antisense oligomer may be selected from the group comprising of any one or more of SEQ ID NOs: 1-60; more preferably SEQ ID NOs: 5, 9, 13, 16-18, 20-27, 30, 32, 42, 49-52, 54-55 and 57; even more preferably SEQ ID NOs: 5, 22, 23, 25, 30 and 57, and combinations or cocktails thereof.

There is also provided a method for manipulating translation of the OPA1 gene transcript, the method including the step of:

a) providing one or more of the antisense oligomers as described herein and allowing the oligomer(s) to bind to a target nucleic acid site.

There is also provided a pharmaceutical, prophylactic, or therapeutic composition to treat, prevent or ameliorate the effects of a disease related to OPA1 expression in a patient, the composition comprising:

a) one or more antisense oligomers as described herein and b) one or more pharmaceutically acceptable carriers and/ or diluents.

Preferably the disease associated with OPA1 expression is associated with decreased levels of functional OPA1 protein expression. Preferably the decreased functional OPA1 is in patients who have ADOA, more preferably in ADOA where OPA1 haploinsufficiency is implicated.

There is also provided a method to treat, prevent or ameliorate the effects of a disease associated with OPA1 expression, comprising the step of:

a) administering to the patient an effective amount of one or more antisense oligomers or pharmaceutical composition comprising one or more antisense oligomers as described herein.

There is also provided the use of purified and isolated antisense oligomers as described herein, for the manufacture of a medicament to treat, prevent or ameliorate the effects of a disease associated with OPA1 expression.

There is also provided a kit to treat, prevent or ameliorate the effects of a disease associated with OPA1 expression in a patient, which kit comprises at least an antisense oligomer as described herein and combinations or cocktails thereof, packaged in a suitable container, together with instructions for its use.

Preferably the disease associated with OPA1 expression in a patient is Autosomal Dominant Optic Atrophy (ADOA). The subject with the disease associated with OPA1 expression may be a mammal, including a human.

Further aspects of the invention will now be described with reference to the accompanying non-limiting examples and drawings.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which.

The band intensity of OPA1 expression was normalised to Beta-actin at 24 hr (B) and 48 hr (D) (assessed by imageJ™). The expression of OPA1 in untreated cells was set to 1 (B, D).

FIG. 5 shows screening of PMOs (50 and 100 μM) in ADOA patient fibroblasts. The western blot gel image shows OPA1 expression in patient fibroblasts transfected with PMOs targeting the OPA1 5' UTR at 48 hr (A). Bar graph represents mean±SEM of OPA1 protein expression (n=1-8 independent experiments). The band intensity of OPA1 expression was normalised to Beta-actin (assessed by imageJ™). The expression of OPA1 in untreated cells was set to 1 (B).

Figure 6:
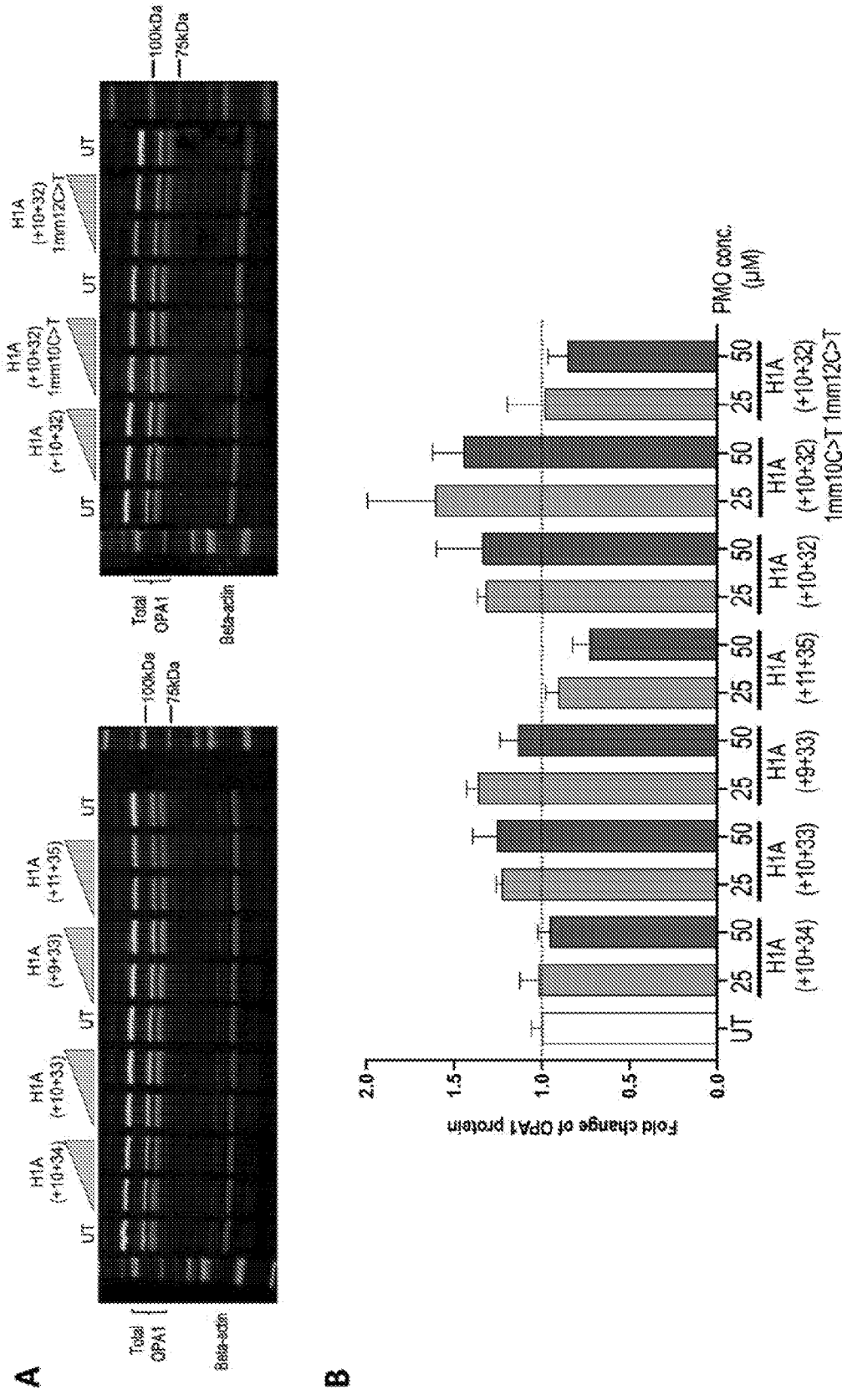

FIG. 6 shows screening of microwalked PMOs adjacent to H1A(+10+32) including deliberate mismatches (25 and 50 μM) in ADOA patient fibroblasts. The western blot gel image shows OPA1 expression in patient fibroblasts transfected with PMOs targeting the OPA1 5' UTR at 48 hr (A). Bar graph represents mean±SEM of OPA1 protein expression (n=2 independent experiments). The band intensity of OPA1 expression was normalised to Beta-actin (assessed by imageJ™). The expression of OPA1 in untreated cells was set to 1 (B)

FIG. 7 shows screening of microwalked PMOs adjacent to H1A(+44+67) including deliberate mismatches (25 and 50 μM) in ADOA patient fibroblasts. The western blot gel image shows OPA1 expression in patient fibroblasts transfected with PMOs targeting the OPA1 5' UTR at 48 hr (A). Bar graph represents mean±SEM of OPA1 protein expression (n=1 independent experiment). The band intensity of OPA1 expression was normalised to Beta-actin (assessed by imageJ™). The expression of OPA1 in untreated cells was set to 1 (B)

Figure 8:
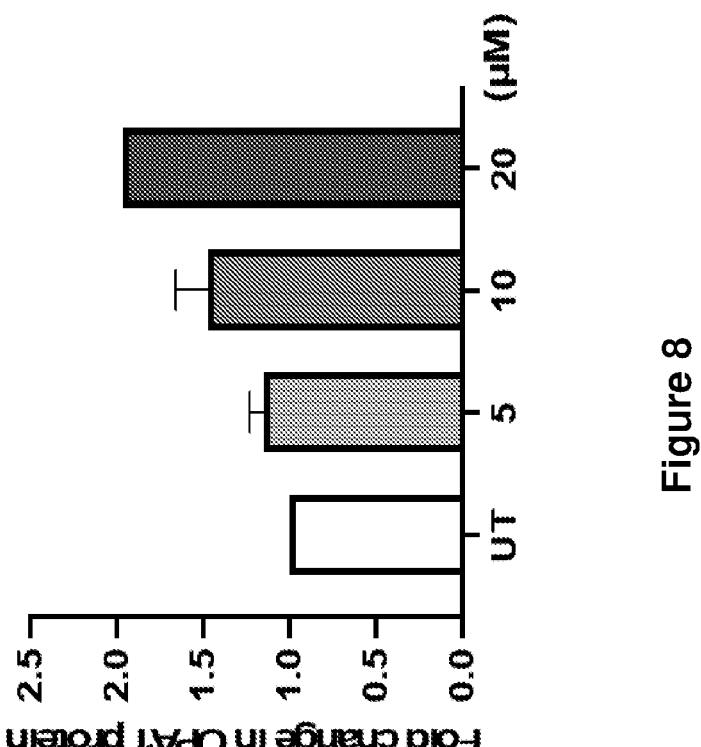

FIG. 8 shows the upregulation of OPA1 protein in ADOA patient fibroblasts following treatment with PPMO H1A(+10+32)

Figure 9:
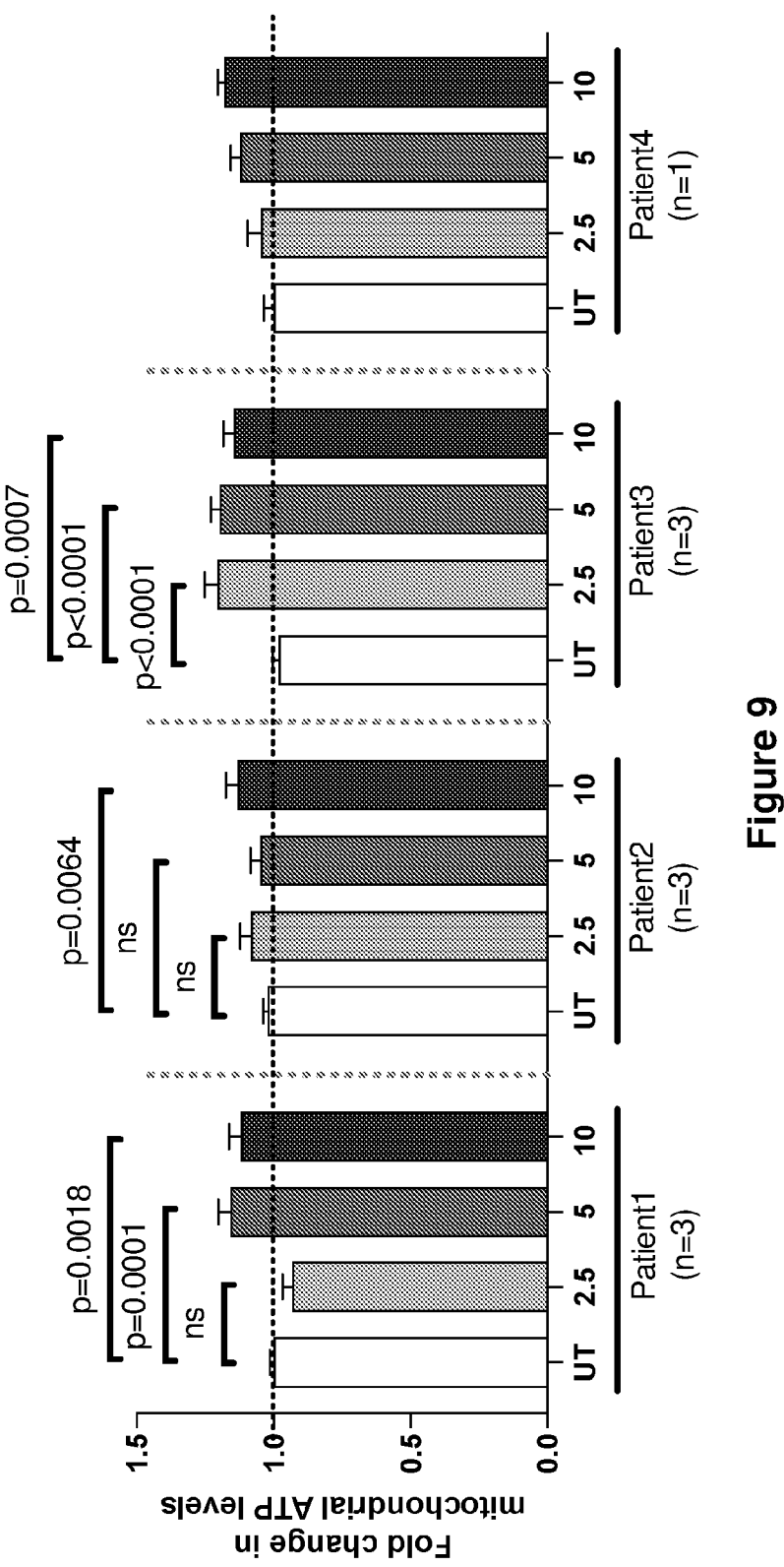

FIG. 9 shows increased in mitochondrial ATP levels in fibroblasts from 4 different ADOA patients following treatment with PPMO H1A(+10+32).

Figure 10:
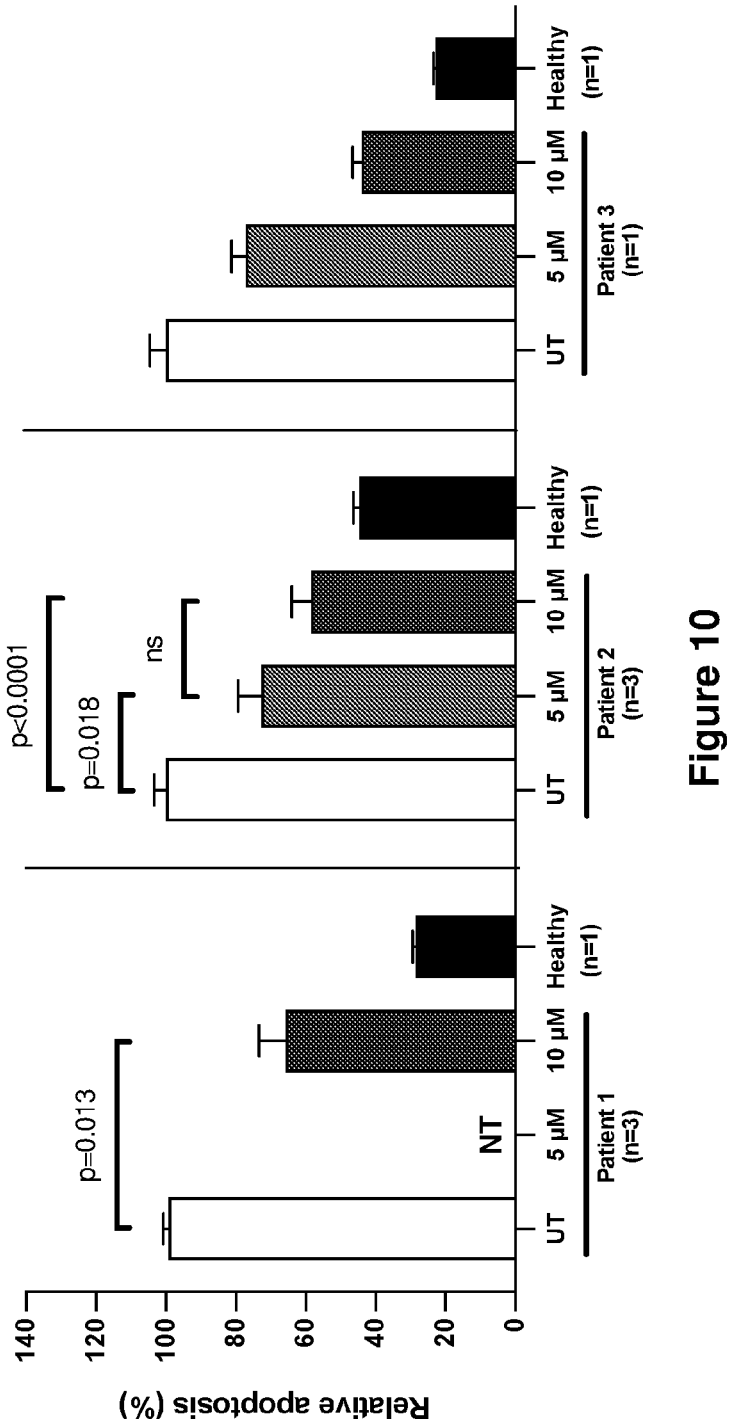

FIG. 10 shows a reduction in relative apoptosis levels in fibroblasts from 3 different ADOA patients following treatment with PPMO H1A(+10+32).

DESCRIPTION OF INVENTION

Detailed Description of the Invention

Antisense Oligonucleotides

ADOA is characterized by degeneration of retinal ganglion cells, and at least 75% of cases are caused by mutations in the OPA1 gene. OPA1 is ubiquitously expressed and is most abundant on the retina. The OPA1 protein is a mitochondrial GTPase that plays an important role in in mitochondrial structure, function and control of apoptosis.

The unique distribution of mitochondria in retinal ganglion cells points to a critical function of this network in retinal ganglion cells and may underlie the sensitivity of these cells to OPA1 loss (also potentially precipitated by exposure of these cells to photo-oxidative stress). The majority of OPA1 mutations (~27% missense, 27% splice variant, 23.5% frameshift, 16.5% nonsense, 6% deletion or duplication) lead to degradation of the transcript by mRNA decay, supporting the hypothesis that haploinsufficiency is a major mechanism underlying ADOA pathogenesis. OPA1 mutations leading to haploinsufficiency cause impaired mitochondrial function including defective complex I-driven ATP synthesis. As ATP is the principal energy currency in cells, insufficient ATP ultimately leads to cellular malfunction and death.

OPA1 haploinsufficiency accounts for a significant proportion of ADOA. OPA1 haploinsufficiency causing ADOA is amenable to treatment by upregulating wild type OPA1.

The 5' untranslated region (5'UTR) is the region of mRNA located immediately upstream from the canonical start codon. The canonical start codon defines the beginning of the main coding sequence (CDS) which is the portion of mRNA that codes for protein. The 5'UTR plays a major role in the control of translation efficiency because it has a key function in ribosome recruitment to the mRNA and determining start codon choice. Upstream open reading frames (uORFs) are mRNA elements which have a start codon in the 5'UTR (non-canonical start codon) with an in-frame stop that is out of frame with the CDS. uORFs are present in approximately half of human transcripts and have been correlated with significantly reduced protein expression of the downstream open reading frame.

The invention provides a means to increase levels of functional OPA1 expression. Preferably the increased functional OPA1 is in patients who have ADOA, more preferably in ADOA where OPA1 haploinsufficiency is implicated.

Without being held to any theory, it is believed that by using antisense oligomers that bind to the uORFs and translation inhibitory elements in the 5'UTRs, the levels of functional OPA1 proteins can be increased. The use of ASOs that bind to and block or alter the uORFs and translation inhibitory elements in the 5'UTRs decreases the translation of out-of-frame main coding sequence and increases the translation of in-frame coding sequences that start from the canonical start codon. The ability of ASOs to selectively increase protein levels by targeting uORFs and translation inhibitory elements in the 5'UTRs of genes provides a means to restore OPA1 protein expression to wildtype levels via a mutation agnostic strategy that is applicable to any mutation in the OPA1 gene leading to disease.

In the present invention, antisense oligomers are also known as antisense oligonucleotides, ASOs, AONs and AONs—the terms are interchangeable.

Broadly, according to one aspect of the invention, there is provided an isolated or purified antisense oligomer that targets the 5'UTR of the OPA1 gene transcript or part thereof. Preferably there is provided an isolated or purified antisense oligomer to increase translation of functional OPA1 protein through steric inhibition of 5'UTR secondary structure elements and/or inhibition of upstream open reading frames. Preferably, there is provided an isolated or purified antisense oligomer for inducing increased production of the OPA1 gene transcript or part thereof.

For example, in one aspect of the invention, there is provided an antisense oligomer of 10 to 50 nucleotides comprising a targeting sequence complementary to a region near or within the 5'UTR of an OPA1 gene transcript or part thereof. In another aspect of the invention, there is provided an antisense oligomer of 10 to 50 nucleotides comprising a targeting sequence complementary to a region near or within an exon of an OPA1 gene transcript or part thereof.

The present invention therefore provides antisense oligonucleotides to disrupt initiation of aberrant translation of an OPA1 gene transcript, or alternatively, through steric inhibition of 5'UTR secondary structure elements, to preferably increase translation commencing at the canonical start codon of OPA1 gene transcript and hence increase levels of functional OPA1 protein.

Broadly, according to one aspect of the invention, there is provided an isolated or purified antisense oligomer designed to hybridise to a uORF of an OPA1 gene transcript or part thereof and disrupt initiation of translation of an OPA1 gene transcript from a non-canonical start site. Antisense oligonucleotides (ASOs) were designed to target the 5' UTR with an aim to sterically inhibit the 5'UTR secondary structure and inhibit selection of the uORF. This disruption will preferably modulate functional OPA1 protein expression by increasing translation of the OPA1 gene transcript from a canonical start site. As translation from a non-canonical start site is more likely to lead to dysfunctional proteins or no translation, and translation from a canonical start site is more likely to lead to functional proteins, the present invention seeks to decrease initiation of translation of an OPA1 gene transcript from a non-canonical start site and/or increase translation of the OPA1 gene transcript from a canonical start site. Either or both of these outcomes will increase the production of OPA1 proteins. Increased OPA1 protein production may assist in treating a disease associated with OPA1 expression (particularly ADOA).

Broadly, according to another aspect of the invention, there is provided an isolated or purified antisense oligomer designed to increase translation of functional OPA1 protein through steric inhibition of 5'UTR secondary structure elements.

For example, in one aspect of the invention, there is provided an antisense oligomer of 10 to 50 nucleotides comprising a targeting sequence complementary to a region near or within the uORF of an OPA1 gene transcript or part thereof. In another aspect of the invention, there is provided an antisense oligomer of 10 to 50 nucleotides comprising a targeting sequence complementary to a region near or within the 5'UTR of an OPA1 gene transcript or part thereof.

The antisense oligomer may be selected from Table 1. Preferably, the antisense oligomer is selected from the list comprising: SEQ ID NOs: 1-60; more preferably SEQ ID NOs: 5, 9, 13, 16-18, 20-27, 30, 32, 42, 49-52, 54-55 and 57; even more preferably SEQ ID NOs: 5, 22, 23, 25, 30 and 57

Preferably the antisense oligomer of the present invention operates to:
   i. hybridise to the 5'UTR of the OPA1 gene transcript and disrupt initiation of aberrant translation of the OPA1 gene transcript or part thereof; and/or
   ii. increase translation of functional OPA1 protein through steric inhibition of 5'UTR secondary structure elements.

Preferably the antisense oligomer of the present invention operates to:
   i. increase mitochondrial ATP levels; and/or
   ii. reduce apoptosis
in the cells of patients with OPA1 mutations.

According to one aspect of the invention, the antisense oligomer may operate to target one or more uORFs of an OPA1 gene transcript or part thereof. For example, the antisense oligomer may bypass a non-canonical start codon in the uORF of an OPA1 gene transcript.

According to another aspect of the invention, the antisense oligomer may operate to target the 5'UTR region of an OPA1 gene transcript or part thereof. For example, the antisense oligomer may enable improved ribosome access to increase translation of functional OPA1 protein.

The antisense oligomer of the present invention may include sequences which can hybridise to such sequences under stringent hybridisation conditions, sequences complementary thereto, sequences containing modified bases, modified backbones, and functional truncations or extensions thereof which possess or modulate translational activity in a gene transcript In certain embodiments, antisense oligomers may be 100% complementary to the target sequence, or may include mismatches, e.g., to accommodate variants, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence.

The invention extends also to a combination of two or more antisense oligomers capable of binding to a selected target to induce increased translation of functional OPA1 protein, including a construct comprising two or more such antisense oligomers. The construct may be used for an antisense oligomer-based therapy.

The invention extends, according to a still further aspect thereof, to cDNA or cloned copies of the antisense oligomer sequences of the invention, as well as to vectors containing the antisense oligomer sequences of the invention. The invention extends further also to cells containing such sequences and/or vectors.

By "isolated" is meant material that is substantially or essentially free from components that normally accompany it in its native state. For example, an "isolated polynucleotide" or "isolated oligonucleotide," as used herein, may refer to a polynucleotide that has been purified or removed from the sequences that flank it in a naturally occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

An antisense oligomer can be said to be "directed to" or "targeted against" a target sequence with which it hybridizes. In certain embodiments, the target sequence includes a region including a uORF, the 5'UTR of mRNA, or other sequences involved in the regulation of translation. The target sequence may be within one or more uORFs or outside of a uORF/5'UTR region or spanning a uORF junction.

In certain embodiments, the antisense oligomer has sufficient sequence complementarity to a target RNA (i.e., the RNA for which translation is modulated) to block a region of a target RNA (e.g., mRNA) in an effective manner. In exemplary embodiments, such binding to the 5'UTR which may contain one or more uORFs in an OPA1 transcript.

An antisense oligomer having a sufficient sequence complementarity to a target RNA sequence to bind to parts of the target RNA means that the antisense oligomer has a sequence sufficient to alter the three-dimensional structure of the targeted RNA.

Selected antisense oligomers can be made shorter, e.g., about 12 bases, or longer, e.g., about 50 bases, and include a small number of mismatches, as long as the sequence is sufficiently complementary to effect translation modulation upon hybridization to the target sequence, and optionally forms with the RNA a heteroduplex having a Tm of 45° C. or greater.

Preferably, the antisense oligomer is selected from the group comprising the sequences set forth in Table 1. Preferably, the antisense oligomer is selected from the group comprising the sequences in SEQ ID NOs: 1-60; more preferably SEQ ID NOs: 5, 9, 13, 16-18, 20-27, 30, 32, 42, 49-52, 54-55 and 57; even more preferably SEQ ID NOs: 5, 22, 23, 25, and 57

In certain embodiments, the degree of complementarity between the target sequence and antisense oligomer is sufficient to form a stable duplex. The region of complementarity of the antisense oligomers with the target RNA sequence may be as short as 8-11 bases, but can be 12-15 bases or more, e.g., 10-50 bases, 10-40 bases, 12-30 bases, 12-25 bases, 15-bases, 12-20 bases, or 15-20 bases, including all integers in between these ranges. An antisense oligomer of about 16-17 bases is generally long enough to have a unique complementary sequence. In certain embodiments, a minimum length of complementary bases may be required to achieve the requisite binding Tm, as discussed herein.

In certain embodiments, oligonucleotides as long as 50 bases may be suitable, where at least a minimum number of bases, e.g., 10-12 bases, are complementary to the target sequence. In general, however, facilitated or active uptake in cells is optimized at oligonucleotide lengths of less than about 30 bases. For phosphorodiamidate morpholino oligomer (PMO) antisense oligomers, an optimum balance of binding stability and uptake generally occurs at lengths of 18-25 bases. Included are antisense oligomers (e.g., CPP-PMOs, PPMOs, PMOs, PMO-X, PNAs, LNAs, 2'-OMe, 2'MOE, 2'F oligomer, thiomorpholino and other hybrid oligomer chemistries) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 bases. PMO—phosphorodiamidate morpholino oligomer; CPP—cell penetrating peptide; PPMO—peptide-conjugated phosphorodiamidate morpholino oligomer; PNA—peptide nucleic acid; LNA—locked nucleic acid; 2'-OMe—2'O-methyl-modified oligomer; 2'MOE—2'-O-methoxy ethyl oligomer, 2'F—2' Fluoro)

In certain embodiments, antisense oligomers may be 100% complementary to the target sequence, or may include mismatches, e.g., to accommodate variants, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence.

Mismatches, if present, are typically less destabilizing toward the end regions of the hybrid duplex than in the middle. The number of mismatches allowed will depend on the length of the oligonucleotide, the percentage of G:C base pairs in the duplex, and the position of the mismatch(es) in the duplex, according to well understood principles of duplex stability. Although such an antisense oligomer is not necessarily 100% complementary to the target sequence, it is effective to stably and specifically bind to the target sequence, such that the efficiency of mRNA translation is improved.

The stability of the duplex formed between an antisense oligomer and a target sequence is a function of the binding Tm and the susceptibility of the duplex to cellular enzymatic cleavage. The Tm of an oligonucleotide with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide Hybridization Techniques, Methods Enzymol. Vol. 154 pp. 94-107. In certain embodiments, antisense oligomers may have a binding Tm, with respect to a complementary-sequence RNA, of greater than body temperature and preferably greater than about 45° C. or 50° C. Tm's in the range 60-80° C. or greater are also included.

Additional examples of variants include antisense oligomers having about or at least about 70% sequence identity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, over the entire length of any of the sequences provided in Table 1, or any of SEQ ID NOs: 1-60; more preferably SEQ ID NOs: 9, 13, 16-18, 20-27, 30, 32, 42, 49-52, 54-55 and 57; even more preferably SEQ ID NOs: 22, 23, 25, 30 and 57.

More specifically, there is provided an antisense oligomer capable of binding to a selected target site to improve the efficiency of mRNA translation in an OPA1 gene transcript or part thereof. The antisense oligomer is preferably selected from those provided in Table 1 or SEQ ID NOs: 1-60; more preferably SEQ ID NOs: 5, 9, 13, 16-18, 20-27, 30, 32, 42, 49-52, 54-55 and 57; even more preferably SEQ ID NOs: 5, 22, 23, 25, 30 and 57.

The modification of mRNA translation preferably enables or alters ribosome access to the OPA1 gene transcript to enable preferential ribosome binding to the canonical start codon.

The modification of mRNA translation of the present invention, using antisense oligomers, may alter ribosome access to one part of the uORF and/or 5'UTR region or may alter ribosome access to two or more parts of the uORF and/or 5'UTR region at once.

The antisense oligomers of the invention may be a combination of two or more antisense oligomers capable of binding to a selected target to induce altered translation of an OPA1 gene transcript. The combination may be a cocktail of two or more antisense oligomers and/or a construct comprising two or more antisense oligomers joined together.

TABLE 1

List of antisense oligonucleotide sequences used in this study. The efficiency score of PMO-induced OPA1 upregulation; 1; greater than 1.1-fold OPA1 upregulation, 0; No OPA1 upregulation, -1; OPA1 downregulation

| SEQ ID | Coordinates | Sequence 5'→3' | Length | Efficacy |
|---|---|---|---|---|
| 1 | OPA1_H1A(-39 -17) | ACCAGCGCATGGGCACAGTGCGT | 23 | 0 |
| 2 | OPA1_H1A(-35 -14) | AGGACCAGCGCATGCGCACAGT | 22 | 0 |
| 3 | OPA1_H1A(-26 -6)1mm | GTCCGCTGAGGACCAGCGCAT | 21 | -1 |
| 4 | OPA1_H1A(-3 +18) | TTTCTAGGCGGGCAGCACGAA | 21 | -1 |
| 5 | OPA1_H1A(+10 +32) | CAACCACTTCACCCTTTCTAGGC | 23 | 1 |
| 6 | OPA1_H1A(+13 +31) | AACCACTTCACCCTTTCTA | 19 | 0 |
| 7 | OPA1_H1A(+33 +57) | ACCCGTACTCAGTCCGTCACGGAAA | 25 | -1 |
| 8 | OPA1_H1A(+33 +54) | CGTACTCAGTCCGTCACGGAAA | 22 | 0 |
| 9 | OPA1_H1A(+56 +80) | ACTTCCGCAAGAGCCTGACAGGCAC | 25 | 1 |
| 10 | hOPA1_H1A(+63 +82) | GGACTTCCGCAAGAGCCTGA | 20 | 0 |
| 11 | OPA1_H1A(+68 +92) | CAATGGCGCATGGACTTCCGCAAGA | 25 | -1 |
| 12 | OPA1_H1A(+78 +98) | CTCCCAATGGCGCATGGACT | 20 | 0 |
| 13 | OPA1_H1A(+128 +146)1mm | CCCAGGAAGTGGTCCTCAG | 19 | 1 |
| 14 | OPA1_H1A(+148 +166) | GGCTCCCGGTCCAGGAATG | 19 | -1 |
| 15 | OPA1_H1A(+200 +218)2mm | TCACGCAGGTGCTGAGACG | 19 | 0 |
| 16 | hOPA1_H1A(-30 -9)2mmT(C > T) | CGTGGAGGACCAGTGCATGCGC | 22 | 1 |
| 17 | hOPA1_H1A(-22 -2) | AACGGTCCGCGGAGGACCAGC | 21 | 1 |
| 18 | hOPA1_H1A(-18 +4) | GCACGAACGGTCCGCGGAGGAC | 22 | 1 |
| 19 | hOPA1_H1A(-14 +8)2mmT(C > T) | GGCAGTACGAACGGTCTGCGGA | 22 | 0 |
| 20 | hOPA1_H1A(-10 +12)2mmT(C > T) | GGTGGGCAGCACGAATGGTCCG | 22 | 1 |
| 21 | hOPA1_H1A(-6 +16) | TCTAGGCGGGCAGCACGAACGG | 22 | 1 |
| 22 | hOPA1_H1A(-2 +21) | CCTTTCTAGGCGGGCAGCACGA | 22 | 1 |
| 23 | hOPA1_H1A(+2 +25) | TCACCCTTTCTAGGCGGGCAGC | 22 | 1 |

TABLE 1-continued

List of antisense oligonucleotide sequences used in this study. The efficiency score of PMO-induced
OPA1 upregulation; 1; greater than 1.1-fold OPA1 upregulation, 0; No OPA1 upregulation, -1;
OPA1 downregulation

| SEQ ID | Coordinates | Sequence 5'→3' | Length | Efficacy |
|---|---|---|---|---|
| 24 | hOPA1_H1A(+7 +31) | AACCACTTCACCCTTTCTAGGCGGG | 25 | 1 |
| 25 | hOPA1_H1A(+12 +36) | GAAACAACCACTTCACCCTTTCTAG | 25 | 1 |
| 26 | hOPA1_H1A(+17 +41) | TCACGGAAACAACCACTTCACCCTT | 25 | 1 |
| 27 | hOPA1_H1A(+22 +46) | GTCCGTCACGGAAACAACCACTTCA | 25 | 1 |
| 28 | hOPA1_H1A(+27 +51) | ACTCAGTCCGTCACGGAAACAACCA | 25 | 0 |
| 29 | hOPA1_H1A(+38 +62) | CAGGCACCCGTACTCAGTCCGTCAC | 25 | 0 |
| 30 | hOPA1_H1A(+44 +67) | CCTGACAGGCACCCGTACTCAGTCC | 25 | 1 |
| 31 | hOPA1_H1A(+50 +71) | GAGCCTGACAGGCACCCGTACTC | 23 | -1 |
| 32 | hOPA1_H1A(+56 +75) | GCAAGAGCCTGACAGGCACCCG | 22 | 1 |
| 33 | hOPA1_H1A(+120 +141) | AAGTGGCCCTCAGCAGCAAGGG | 22 | -1 |
| 34 | hOPA1_H1A(+125 +148)2mmT(C > T) | ACCTAGGAAGTGGTCCTCAGCAGC | 24 | -1 |
| 35 | hOPA1_H1A(+129 +154) | GGAATGACCCAGGAAGTGGCCCTCA | 25 | -1 |
| 36 | hOPA1_H1A(+134 +159) | GTCCAGGAATGACCCAGGAAGTGGC | 25 | -1 |
| 37 | hOPA1_H1A(+42 +66) | CTGACAGGCACCCGTACTCAGTCCG | 25 | 0 |
| 38 | hOPA1_H1A(+44 +68) | GCCTGACAGGCACCCGTACTCAGTC | 25 | 0 |
| 39 | hOPA1_H1A(+45 +69) | AGCCTGACAGGCACCCGTACTCAGT | 25 | -1 |
| 40 | hOPA1_H1A(+46 +70) | GAGCCTGACAGGCACCCGTACTCAG | 25 | 0 |
| 41 | hOPA1_H1A(+47 +71) | AGAGCCTGACAGGCACCCGTACTCA | 25 | 0 |
| 42 | hOPA1_H1A(+48 +72) | AAGAGCCTGACAGGCACCCGTACTC | 25 | 1 |
| 43 | hOPA1_H1A(+49 +73) | CAAGAGCCTGACAGGCACCCGTACT | 25 | 0 |
| 44 | hOPA1_H1A(+50 +74) | GCAAGAGCCTGACAGGCACCCGTAC | 25 | 0 |
| 45 | hOPA1_H1A(+42 +66)2mmC > T | CTGACAGGCATTCGTACTCAGTCCG | 25 | -1 |
| 46 | hOPA1_H1A(+44 +68)2mmC > T | GCCTGACAGGCACTTGTACTCAGTC | 25 | 0 |
| 47 | hOPA1_H1A(+45 +69)2mmC > T | AGCCTGACAGGCATTCGTACTCAGT | 25 | 0 |
| 48 | hOPA1_H1A(+46 +70)2mmC > T | GAGCTTGACAGGCACCTGTACTCAG | 25 | 0 |
| 49 | hOPA1_H1A(+47 +71)2mmC > T | AGAGCTTGACAGGCACTCGTACTCA | 25 | 1 |
| 50 | hOPA1_H1A(+48 +72)2mmC > T | AAGAGCTTGACAGGCACTCGTACTC | 25 | 1 |
| 51 | hOPA1_H1A(+49 +73)2mmC > T | CAAGAGCTTGACAGGCATCCGTACT | 25 | 1 |
| 52 | hOPA1_H1A(+50 +74)2mmC > T | GCAAGAGCTTGACAGGCATCCGTAC | 25 | 1 |
| 53 | OPA1_H1A(+10 +34) | AACAACCACTTCACCCTTTCTAGGC | 25 | 0 |
| 54 | OPA1_H1A(+10 +33) | ACAACCACTTCACCCTTTCTAGGC | 24 | 1 |
| 55 | OPA1_H1A(+9 +33) | ACAACCACTTCACCCTTTCTAGGCG | 25 | 1 |
| 56 | OPA1_H1A(+11 +35) | AAACAACCACTTCACCCTTTCTAGG | 25 | -1 |
| 57 | OPA1_H1A(+10 +32)1mm10C > T | CAACCACTTACCCTTTCTAGGC | 23 | 1 |
| 58 | OPA1_H1A(+10 +32)1mm12C > T | CAACCACTTCATCCTTTCTAGGC | 23 | 0 |
| 59 | hOPA1_H1A(+63 +80) | ACTTCCGCAAGAGCCTGA | 18 | 0 |
| 60 | hOPA1_H1A(+79 +96) | TCCCAATGGCGCATGGAC | 18 | -1 |

There is also provided a method for modulating translation of an OPA1 gene transcript, the method including the step of:

a) providing one or more of the antisense oligomers as described herein and allowing the oligomer(s) to bind to a target nucleic acid site.

According to yet another aspect of the invention, there is provided a translation manipulation target nucleic acid sequence for OPA1 comprising the DNA equivalents of the nucleic acid sequences selected from Table 1 or the group consisting of SEQ ID NOs: 1-60; more preferably SEQ ID NOs: 5, 9, 13, 16-18, 20-27, 30, 32, 42, 49-52, 54-55 and 57; even more preferably SEQ ID NOs: 5, 22, 23, 25, 30, and 57, and sequences complementary thereto.

Designing antisense oligomers to completely mask consensus uORF regulatory elements may not necessarily generate a change in translation of the targeted gene transcript. Furthermore, the inventors have discovered that size or length of the antisense oligomer itself is not always a primary factor when designing antisense oligomers. With some targets, antisense oligomers as short as 20 bases were able to induce some change in translation, in certain cases more efficiently than other longer (eg 25 bases) oligomers directed to the same regulatory element.

The inventors have also discovered that there does not appear to be any standard motif that can be blocked or masked by antisense oligomers to redirect translation. It has been found that antisense oligomers must be designed, and their individual efficacy evaluated empirically.

More specifically, the antisense oligomer may be selected from those set forth in Table 1. The sequences are preferably selected from the group consisting of any one or more of SEQ ID NOs: 1-60; more preferably SEQ ID NOs: 5, 9, 13, 16-18, 20-27, 30, 32, 42, 49-52, 54-55 and 57; even more preferably SEQ ID NOs: 5, 22, 23, 25, 30 and 57, and combinations or cocktails thereof. This includes sequences which can hybridise to such sequences under stringent hybridisation conditions, sequences complementary thereto, sequences containing modified bases, modified backbones, and functional truncations or extensions thereof which possess or modulate mRNA translating activity in an OPA1 gene transcript.

The oligomer and the DNA, cDNA or RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or pairing such that stable and specific binding occurs between the oligomer and the DNA, cDNA or RNA target. It is understood in the art that the sequence of an antisense oligomer need not be 100% complementary to that of its target sequence to be specifically hybridisable. An antisense oligomer is specifically hybridisable when binding of the compound to the target DNA or RNA molecule interferes with the normal function of the target DNA or RNA product, and there is a sufficient degree of complementarity to avoid non-specific binding of the antisense oligomer to non-target sequences under conditions in which specific binding is desired, i.e., under physiological conditions in the case of in vivo assays or therapeutic treatment, and in the case of in vitro assays, under conditions in which the assays are performed.

Selective hybridisation may be under low, moderate or high stringency conditions, but is preferably under high stringency. Those skilled in the art will recognise that the stringency of hybridisation will be affected by such conditions as salt concentration, temperature, or organic solvents, in addition to the base composition, length of the complementary strands and the number of nucleotide base mismatches between the hybridising nucleic acids. Stringent temperature conditions will generally include temperatures in excess of 30° C., typically in excess of 37° C., and preferably in excess of 45° C., preferably at least 50° C., and typically 60° C.-80° C. or higher. Stringent salt conditions will ordinarily be less than 1000 mM, typically less than 500 mM, and preferably less than 200 mM. However, the combination of parameters is much more important than the measure of any single parameter. An example of stringent hybridisation conditions is 65° C. and 0.1×SSC (1×SSC=0.15 M NaCl, 0.015 M sodium citrate pH 7.0). Thus, the antisense oligomers of the present invention may include oligomers that selectively hybridise to the sequences provided in Table 1, or SEQ ID NOs: 1-more preferably SEQ ID NOs: 5, 9, 13, 16-18, 20-27, 30, 32, 42, 49-52, 54-55 and 57; even more preferably SEQ ID NOs: 5, 22, 23, 25, 30 and 57.

Typically, selective hybridisation will occur when there is at least about 55% identity over a stretch of at least about 14 nucleotides, preferably at least about 65%, more preferably at least about 75% and most preferably at least about 90%, 95%, 98% or 99% identity with the nucleotides of the antisense oligomer. The length of identity comparison, as described, may be over longer stretches and in certain embodiments will often be over a stretch of at least about nine nucleotides, usually at least about 12 nucleotides, more usually at least about often at least about 21, 22, 23 or 24 nucleotides, at least about 25, 26, 27 or 28 nucleotides, at least about 29, 30, 31 or 32 nucleotides, at least about 36 or more nucleotides.

Thus, the antisense oligomer sequences of the invention preferably have at least 75%, more preferably at least 85%, more preferably at least 86, 87, 88, 89 or 90% homology to the sequences shown in the sequence listings herein. More preferably there is at least 91, 92, 93 94, or 95%, more preferably at least 96, 97, 98% or 99%, identity. Generally, the shorter the length of the antisense oligomer, the greater the identity required to obtain selective hybridisation. Consequently, where an antisense oligomer of the invention consists of less than about 30 nucleotides, it is preferred that the percentage identity is greater than 75%, preferably greater than 85, 86, 87, 88, 89, 90, 91, 92, 93, 94, 95%, 96, 97, 98% or 99% compared with the antisense oligomers set out in the sequence listings herein. Nucleotide identity comparisons may be conducted by sequence comparison programs such as the GCG Wisconsin Bestfit program or GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

The antisense oligomer of the present invention may have regions of reduced identity, and regions of exact identity with the target sequence. It is not necessary for an oligomer to have exact identity for its entire length. For example, the oligomer may have continuous stretches of at least 4 or 5 bases that are identical to the target sequence, preferably continuous stretches of at least 6 or 7 bases that are identical to the target sequence, more preferably continuous stretches of at least 8 or 9 bases that are identical to the target sequence. The oligomer may have stretches of at least 10, 11, 12, 13, 14, 15, 16, 17, 18, 19, 20, 21, 22, 23, 24, 25 or 26 bases that are identical to the target sequence. The remaining stretches of oligomer sequence may be intermittently identical with the target sequence; for example, the remaining sequence may have an identical base, followed by a non-identical base, followed by an identical base. Alternatively (or as well) the oligomer sequence may have several stretches of identical sequence (for example 3, 4, 5 or 6 bases) interspersed with stretches of less than perfect identity. Such sequence mismatches will preferably have no or very little loss of translation modulating activity. Even more preferably, such sequence mismatches will have increased translation modulating activity.

The term "modulate" or "modulates" includes to "increase" or "decrease" one or more quantifiable parameters, optionally by a defined and/or statistically significant amount. The terms "increase" or "increasing," "enhance" or "enhancing," or "stimulate" or "stimulating", or "augment" or "augmenting" refer generally to the ability of one or more antisense oligomers or compositions to produce or cause a greater physiological response (i.e., downstream effects) in a cell or a subject relative to the response caused by either no antisense oligomer or a control compound. The terms "decreasing" or "decrease" refer generally to the ability of one or antisense oligomers or compositions to produce or cause a reduced physiological response (i.e., downstream effects) in a cell or a subject relative to the response caused by either no antisense oligomer or a control compound.

Relevant physiological or cellular responses (in vivo or in vitro) will be apparent to persons skilled in the art and may include increases in the expression of functional OPA1 protein in a cell, tissue, or subject in need thereof. An "increased" or "augmented" amount may be a statistically significant amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1, e.g., 1.5, 1.6, 1.7. 1.8) more than the amount produced when no antisense oligomer is present (the absence of an agent) or a control compound is used.

The term "reduce" or "inhibit" may relate generally to the ability of one or more antisense oligomers or compositions to "decrease" a relevant physiological or cellular response, such as a symptom of a disease described herein, as measured according to routine techniques in the diagnostic art. Relevant physiological or cellular responses (in vivo or in vitro) will be apparent to persons skilled in the art, and may include reductions in the symptoms or pathology of a disease such as ADOA.

A "decrease" in a response may be statistically significant as compared to the response produced by no antisense oligomer or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

The length of an antisense oligomer may vary, as long as it is capable of binding selectively to the intended location within the mRNA molecule. The length of such sequences can be determined in accordance with selection procedures described herein. Generally, the antisense oligomer will be from about 10 nucleotides in length, up to about 50 nucleotides in length. It will be appreciated, however, that any length of nucleotides within this range may be used in the method. Preferably, the length of the antisense oligomer is between 10 and 40, 10 and 35, 15 to 30 nucleotides in length or 20 to 30 nucleotides in length, most preferably about to 30 nucleotides in length. For example, the oligomer may be 20, 21, 22, 23, 24, 25, 26, 27, 28, 29 or 30 nucleotides in length.

As used herein, an "antisense oligomer" refers to a linear sequence of nucleotides, or nucleotide analogs, that allows the nucleobase to hybridize to a target sequence in an RNA by Watson-Crick base pairing, to form an oligonucleotide: RNA heteroduplex within the target sequence. The terms "antisense oligomer", "antisense oligonucleotide", "oligomer" and "antisense compound" may be used interchangeably to refer to an oligonucleotide. The cyclic subunits may be based on ribose or another pentose sugar or, in certain embodiments, a morpholino group (see description of morpholino oligonucleotides below). Also contemplated are peptide nucleic acids (PNAs), locked nucleic acids (LNAs), and 2'-O-methyl oligonucleotides, among other antisense agents known in the art.

Included are non-naturally occurring antisense oligomers, or "oligonucleotide analogs", including antisense oligomers or oligonucleotides having (i) a modified backbone structure, e.g., a backbone other than the standard phosphodiester linkage found in naturally occurring oligo- and polynucleotides, and/or (ii) modified sugar moieties, e.g., morpholino moieties rather than ribose or deoxyribose moieties. Oligonucleotide analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

One method for producing antisense oligomers is the methylation of the 2' hydroxyribose position and the incorporation of a phosphorothioate backbone produces molecules that superficially resemble RNA but that are much more resistant to nuclease degradation, although persons skilled in the art of the invention will be aware of other forms of suitable backbones that may be useable in the objectives of the invention.

To avoid degradation of pre-mRNA and/or mRNA during duplex formation with the antisense oligomers, the antisense oligomers used in the method may be adapted to minimise or prevent cleavage by endogenous RNase H. This property is highly preferred, as the treatment of the RNA with the unmethylated oligomers, either intracellular or in crude extracts that contain RNase H, leads to degradation of the pre-mRNA:antisense and/or mRNA:antisense oligomer duplexes. Any form of modified antisense oligomers that is capable of by-passing or not inducing such degradation may be used in the present method. The nuclease resistance may be achieved by modifying the antisense oligomers of the invention so that it comprises partially unsaturated aliphatic hydrocarbon chain and one or more polar or charged groups including carboxylic acid groups, ester groups, and alcohol groups.

Antisense oligomers that do not activate RNase H can be made in accordance with known techniques (see, e.g., U.S. Pat. No. 5,149,797). Such antisense oligomers, which may be deoxyribonucleotide or ribonucleotide sequences, simply contain any structural modification which sterically hinders or prevents binding of RNase H to a duplex molecule containing the oligomer as one member thereof, which structural modification does not substantially hinder or disrupt duplex formation. Because the portions of the oligomer involved in duplex formation are substantially different from those portions involved in RNase H binding thereto, numerous antisense oligomers that do not activate RNase H are available. For example, such antisense oligomers may be oligomers wherein at least one, or all, of the inter-nucleotide bridging phosphate residues are modified phosphates, such as methyl phosphonates, methyl phosphorothioates, phosphoromorpholidates, phosphoropiperazidates boranophosphates, amide linkages and phosphoramidates. For example, every other one of the internucleotide bridging phosphate residues may be modified as described. In another non-limiting example, such antisense oligomers are molecules wherein at least one, or all, of the nucleotides contain a 2' lower alkyl moiety (such as, for example, C1-C4, linear or branched, saturated or unsaturated alkyl, such as methyl, ethyl, ethenyl, propyl, 1-propenyl, 2-propenyl, and isopropyl). For example, every other one of the nucleotides may be modified as described.

An example of antisense oligomers which when duplexed with RNA are not cleaved by cellular RNase H is 2'-O-methyl derivatives. Such 2'-O-methyl-oligoribonucleotides are stable in a cellular environment and in animal tissues, and their duplexes with RNA have higher Tm values than their ribo- or deoxyribo-counterparts. Alternatively, the nuclease resistant antisense oligomers of the invention may have at least one of the last 3'-terminus nucleotides fluoridated. Still alternatively, the nuclease resistant antisense oligomers of the invention have phosphorothioate bonds linking between at least two of the last 3-terminus nucleotide bases, preferably having phosphorothioate bonds linking between the last four 3'-terminal nucleotide bases.

Increased modulation of translation may also be achieved with alternative oligonucleotide chemistry. For example, the antisense oligomer may be chosen from the list comprising: phosphoramidate or phosphorodiamidate morpholino oligomer (PMO); PMO-X; PPMO; peptide nucleic acid (PNA); a locked nucleic acid (LNA) and derivatives including alpha-L-LNA, 2'-amino LNA, 4'-methyl LNA and 4'-O-methyl LNA; ethylene bridged nucleic acids (ENA) and their derivatives; phosphorothioate oligomer; tricyclo-DNA oligomer (tcDNA); tricyclophosphorothioate oligomer; 2'-O-methyl-modified oligomer (2'-O-Me); 2'-O-methoxy ethyl (2'-MOE); 2'-fluoro (2'F), 2'-fluroarabino (FANA); unlocked nucleic acid (UNA); hexitol nucleic acid (HNA); cyclohexenyl nucleic acid (CeNA); 2'-amino (2'—NH2); 2'-O-ethyleneamine or any combination of the foregoing as mixmers or as gapmers. To further improve the delivery efficacy, the above-mentioned modified nucleotides are often conjugated with fatty acids/lipid/cholesterol/amino acids/carbohydrates/polysaccharides/nanoparticles etc. to the sugar or nucleobase moieties. These conjugated nucleotide derivatives can also be used to construct exon skipping antisense oligomers. Antisense oligomer-induced translation modulation of the human OPA1 gene transcripts have generally used either oligoribonucleotides, PNAs, 2'-O-Me or MOE modified bases on a phosphorothioate backbone. Although 2'-O-Me ASOs are used for oligo design, due to their efficient uptake in vitro when delivered as cationic lipoplexes, these compounds are susceptible to nuclease degradation and are not considered ideal for in vivo or clinical applications. When alternative chemistries are used to generate the antisense oligomers of the present invention, the thymine (T) of the sequences provided herein may be replaced by a uracil (U).

While the antisense oligomers described above are a preferred form of the antisense oligomers of the present invention, the present invention includes other oligomeric antisense molecules, including but not limited to oligomer mimetics such as are described below.

Specific examples of preferred antisense oligomers useful in this invention include oligomers containing modified backbones or non-natural inter-nucleoside linkages. As defined in this specification, oligomers having modified backbones include those that retain a phosphorus atom in the backbone and those that do not have a phosphorus atom in the backbone. For the purposes of this specification, and as sometimes referenced in the art, modified oligomers that do not have a phosphorus atom in their inter-nucleoside backbone can also be considered to be antisense oligomers.

In other preferred oligomer mimetics, both the sugar and the inter-nucleoside linkage, i.e., the backbone, of the nucleotide units are replaced with novel groups. The base units are maintained for hybridization with an appropriate nucleic acid target compound. One such oligomeric compound, an oligomer mimetic that has been shown to have excellent hybridization properties, is referred to as a peptide nucleic acid (PNA). In PNA compounds, the sugar-backbone of an oligomer is replaced with an amide containing backbone, in particular an aminoethylglycine backbone. The nucleo-bases are retained and are bound directly or indirectly to aza nitrogen atoms of the amide portion of the backbone.

Another preferred chemistry is the phosphorodiamidate morpholino oligomer (PMO) oligomeric compounds, which are not degraded by any known nuclease or protease. These compounds are uncharged, and do not activate RNase H activity when bound to an RNA strand.

Modified oligomers may also contain one or more substituted sugar moieties. Oligomers may also include nucleobase (often referred to in the art simply as "base") modifications or substitutions. Certain nucleobases are particularly useful for increasing the binding affinity of the oligomeric compounds of the invention. These include 5-substituted pyrimidines, 6-azapyrimidines, and N-2, N-6 and O-6 substituted purines, including 2-aminopropyladenine, 5-propynyluracil and 5-propynylcytosine. 5-methyl-cytosine substitutions have been shown to increase nucleic acid duplex stability by 0.6-1.2° C., even more particularly when combined with 2'-O-methoxyethyl sugar modifications.

Another modification of the oligomers of the invention involves chemically linking to the oligomer one or more moieties or conjugates that enhance the activity, cellular distribution or cellular uptake of the oligomer. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, myristyl, or an octadecylamine or hexylamino-carbonyl-oxycholesterol moiety.

Cell penetrating peptides have been added to phosphorodiamidate morpholino oligomers to enhance cellular uptake and nuclear localization. Different peptide tags have been shown to influence efficiency of uptake and target tissue specificity, as shown in Jearawiriyapaisarn et al. (2008), Mol. Ther. 16 9, 1624-1629.

It is not necessary for all positions in a given compound to be uniformly modified, and in fact more than one of the aforementioned modifications may be incorporated in a single compound or even at a single nucleoside within an oligomer. The present invention also includes antisense oligomers that are chimeric compounds. "Chimeric" antisense oligomers or "chimeras," in the context of this invention, are antisense oligomers, particularly oligomers, which contain two or more chemically distinct regions, each made up of at least one monomer unit, i.e., a nucleotide in the case of an oligomer compound. These oligomers typically contain at least one region wherein the oligomer is modified so as to confer upon the oligomer or antisense oligomer increased resistance to nuclease degradation, increased cellular uptake, and an additional region for increased binding affinity for the target nucleic acid.

The activity of antisense oligomers and variants thereof can be assayed according to routine techniques in the art. The expression levels of surveyed RNAs and proteins may be assessed by any of a wide variety of well-known methods for detecting expression of a transcribed nucleic acid or protein. Non-limiting examples of such methods include RT-PCR of spliced forms of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays. Protein expression levels can be assessed by western blot and/or ELISA assays from a cell, tissue or organism, and by assessing downstream functional or physiological effects.

If two or more different sized transcripts are present, the resulting proteins may be assessed by any of a wide variety of well-known methods for detecting the expression of the relevant protein. Non-limiting examples of such methods include immunological methods for detection of proteins; protein purification methods; mass spectrometry; and protein function or activity assays.

The present invention provides antisense oligomer induced translation modulation of the OPA1 gene transcript, clinically relevant oligomer chemistries and delivery systems to direct functional OPA1 protein to therapeutic levels. Clinically relevant increases in the amount of functional OPA1 translation, and hence OPA1 protein from OPA1 gene transcription, are achieved by:

1) oligomer refinement in vitro using fibroblast cell lines, through experimental assessment of (i) target motifs, (ii) antisense oligomer length and development of oligomer cocktails, (iii) choice of chemistry, and (iv) the addition of cell-penetrating peptides (CPP) to enhance oligomer delivery; and 2) detailed evaluation of a novel approach to modulate OPA1 translation via either ATG or near cognate start codons, inhibition or effective steric hindrance to increase translation.

Modulation of OPA1 translation can be achieved by either translation inhibition of non-primary uORFs (forcing initiation of translation from the maximally efficient primary uORF), or increased translation efficiency due to steric hindrance of the secondary structure. The relative efficacies of each method are not predictable and carry inherent uncertainty around which method would be most effective.

As such, it is demonstrated herein that translation of OPA1 mRNA can be modulated with specific antisense oligomers. In this way functionally significant increases in the amount of OPA1 protein can be obtained, thereby reducing the severe pathology associated with ADOA caused by OPA1 haploinsufficiency.

The antisense oligomers used in accordance with this invention may be conveniently made through the well-known technique of solid phase synthesis. Equipment for such synthesis is sold by several vendors including, for example, Applied Biosystems (Foster City, Calif.). One method for synthesising oligomers on a modified solid support is described in U.S. Pat. No. 4,458,066.

Any other means for such synthesis known in the art may additionally or alternatively be employed. It is well known to use similar techniques to prepare oligomers such as the phosphorothioates and alkylated derivatives. In one such automated embodiment, diethyl-phosphoramidites are used as starting materials and may be synthesized as described by Beaucage, et al., (1981) Tetrahedron Letters, 22:1859-1862.

The antisense oligomers of the invention are synthesised in vitro and do not include antisense compositions of biological origin, or genetic vector constructs designed to direct the in vivo synthesis of antisense oligomers. The molecules of the invention may also be mixed, encapsulated, conjugated or otherwise associated with other molecules, molecule structures or mixtures of compounds, as for example, liposomes, receptor targeted molecules etc.

The antisense oligomers may be formulated for oral, topical, parenteral or other administration, particularly formulations for topical ocular and injectable ocular administration. The formulations may be formulated for assisting in uptake, distribution and/or absorption at the site of administration or activity. Preferably the antisense oligomers of the present invention are formulated for delivered topically to the eye or by intraocular injection or intraocular implant, so that the effects on OPA1 production are spatially limited and are not systemic.

Method of Treatment

According to a still further aspect of the invention, there is provided one or more antisense oligomers as described herein for use in an antisense oligomer-based therapy. Preferably, the therapy is for a disease related to OPA1 expression. More preferably, the therapy for a disease related to OPA1 expression is therapy for ADOA. Preferably the disease associated with OPA1 expression is associated with decreased levels of functional OPA1 protein expression. Preferably the decreased functional OPA1 is in patients who have ADOA, more preferably in ADOA where OPA1 haploinsufficiency is implicated.

More specifically, the antisense oligomer may be selected from Table 1, or the group consisting of any one or more of SEQ ID NOs: 1-60; more preferably SEQ ID NOs: 5, 9, 13, 16-18, 20-27, 30, 32, 42, 49-52, 54-55 and 57; even more preferably SEQ ID NOs: 5, 22, 23, 25, 30 and 57, and combinations or cocktails thereof. This includes sequences which can hybridise to such sequences under stringent hybridisation conditions, sequences complementary thereto, sequences containing modified bases, modified backbones, and functional truncations or extensions thereof which possess or modulate mRNA translation of an OPA1 gene transcript.

The invention extends also to a combination of two or more antisense oligomers capable of binding to a selected target to induce translation modulation in an OPA1 gene transcript. The combination may be a cocktail of two or more antisense oligomers, a construct comprising two or more or two or more antisense oligomers joined for use in an antisense oligomer-based therapy.

There is therefore provided a method to treat, prevent or ameliorate the effects of a disease associated with OPA1 expression, comprising the step of:

a) administering to the patient an effective amount of one or more antisense oligomers or pharmaceutical composition comprising one or more antisense oligomers as described herein.

Preferably the disease associated with OPA1 expression in a patient is ADOA.

Therefore, the invention provides a method to treat, prevent or ameliorate the effects of ADOA, comprising the step of:

a) administering to the patient an effective amount of one or more antisense oligomers or pharmaceutical composition comprising one or more antisense oligomers as described herein.

Preferably, the therapy is used to increase the levels of functional OPA1 protein via a translation modulation strategy. The increase in levels of OPA1 protein is preferably achieved by reducing translation from non-canonical initiating elements in the 5'UTR of the OPA1 gene transcript or part thereof, and/or enabling increased translation from the canonical start codon for OPA1 through altering ribosome access to the OPA1 gene transcript or part thereof.

Preferably administration of the antisense oligomer results in the between 1.1 and 2.5-fold higher expression of the OPA1 protein than the expression of the OPA1 protein in subjects with symptomatic OPA1 mutations.

The increase in functional OPA1 will preferably lead to a reduction in the quantity, duration or severity of the symptoms of an OPA1-related disease, such as ADOA.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease being treated, delaying the onset of that disease, or reducing the severity of its onset. "Treatment" or "prophylaxis" does not necessarily indicate complete eradication, cure, or prevention of the disease, or associated symptoms thereof.

The subject with the disease associated with OPA1 expression may be a mammal, including a human.

The antisense oligomers of the present invention may also be used in conjunction with alternative therapies, such as drug therapies.

The present invention therefore provides a method of treating, preventing or ameliorating the effects of a disease associated with OPA1 expression, wherein the antisense oligomers of the present invention and administered sequentially or concurrently with another alternative therapy associated with treating, preventing or ameliorating the effects of a disease associated with OPA1 expression. Preferably, the disease is ADOA.

Delivery

The antisense oligomers of the present invention also can be used as a prophylactic or therapeutic, which may be utilised for the purpose of treatment of a disease. Accordingly, in one embodiment the present invention provides antisense oligomers that bind to a selected target in the OPA1 mRNA to induce efficient and consistent translation modulation as described herein, in a therapeutically effective amount, admixed with a pharmaceutically acceptable carrier, diluent, or excipient.

There is also provided a pharmaceutical, prophylactic, or therapeutic composition to treat, prevent or ameliorate the effects of a disease related to OPA1 expression in a patient, the composition comprising:

a) one or more antisense oligomers as described herein and b) one or more pharmaceutically acceptable carriers and/or diluents.

Preferably, the antisense oligomer of the present invention is delivered via a localised ocular route to avoid a systemic effect. Routes of administration include, but are not limited to, intravitreal, intracameral, subconjunctival, subtenon, retrobulbar, posterior juxtascleral, or topical (drops, eye washes, creams etc). Delivery methods include, for example, injection by a syringe and a drug delivery device, such as an implanted vitreal delivery device (i.e., VITRASERT®).

More preferably, the antisense oligomer is administered via intravitreal injection at between 0.005-5 mg per eye, 0.005-1 mg per eye, 0.005-0.5 mg per eye, 0.01-5 mg per eye, 0.02-1 mg per eye, 0.01-0.5 mg per eye, 0.01-0.1 mg per eye, 0.01-0.5 mg per eye, 2-20 mg per eye, 0.5-20 mg per eye, or more preferably between 5-20 mg per eye. The antisense oligomer may be administered via intravitreal injection at, for example, about 0.01 mg per eye, 0.02 mg per eye, 0.03 mg per eye, 0.04 mg per eye, 0.05 mg per eye, 0.06 mg per eye, 0.07 mg per eye, 0.08 mg per eye, 0.09 mg per eye, 0.1 mg per eye, 0.2 mg per eye, 0.3 mg per eye, 0.4 mg per eye, 0.5 mg per eye, 1 mg per eye, 2 mg per eye. Preferably, the antisense oligomer is administered via intravitreal injection at about 0.01-0.5 mg per eye.

The antisense oligomer may be administered at regular intervals for a short time period, e.g., daily for two weeks or less. However, in many cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

Dosing may be dependent on severity and responsiveness of the disease state to be treated, with the course of treatment lasting from several days to several months, or until a cure is effected or a diminution of the disease state is achieved. Alternatively, dosing may be titrated against disease progression rate. A baseline progression is established. Then the progression rate after an initial once off dose is monitored to check that there is a reduction in the rate. Preferably, there is no progression after dosing. Preferably, re-dosing is only necessary if progression rate is unchanged. Successful treatment preferably results in no further progression of the disease or even some recovery of vision. Optimal dosing schedules can be calculated from measurements of drug accumulation in the body of the patient. Persons of ordinary skill can easily determine optimum dosages, dosing methodologies and repetition rates.

Optimum dosages may vary depending on the relative potency of individual oligomers and can generally be estimated based on EC50s found to be effective in in vitro and in vivo animal models.

In general, dosage is administered via intravitreal injection at between 0.005-5 mg per eye and may be given once or more daily, weekly, monthly or yearly, or even once every 2 to 20 years. Repetition rates for dosing depend on progression rate of the disease. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, the dose may be administered via intravitreal injection at between 0.005-5 mg per eye, once or more daily, weekly, monthly or yearly, or even once every 2 to 20 years.

An effective in vivo treatment regimen using the antisense oligomers of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of disorder under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligomers of the invention may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of a mutant mRNA in relation to a reference normal mRNA or protein as determined by standard techniques such as RT-PCR, Northern blotting, ELISA or Western blotting.

Intranuclear oligomer delivery is a major challenge for antisense oligomers. Different cell-penetrating peptides (CPP) localize PMOs to varying degrees in different conditions and cell lines, and novel CPPs have been evaluated by the inventors for their ability to deliver PMOs to the target cells. The terms CPP or "a peptide moiety which enhances cellular uptake" are used interchangeably and refer to cationic cell penetrating peptides, also called "transport peptides", "carrier peptides", or "peptide transduction domains". The peptides, as shown herein, have the capability of inducing cell penetration within about or at least about 30%, 40%, 50%, 60%, 70%, 80%, 90%, or 100% of cells of a given cell culture population and allow macromolecular translocation within multiple tissues in vivo upon systemic administration and/or macromolecular translocation when administered intraocularly. CPPs are well-known in the art and are disclosed, for example in U.S. Application No. 2010/0016215, which is incorporated by reference in its entirety.

The present invention therefore provides antisense oligomers of the present invention in combination with cell-penetrating peptides for manufacturing therapeutic pharmaceutical compositions.

Excipients

The antisense oligomers of the present invention are preferably delivered in a pharmaceutically acceptable composition. The composition may comprise about 1 nM to 1000 nM of each of the desired antisense oligomer(s) of the invention. Preferably, the composition may comprise about 1 nM to 500 nM, 10 nM to 500 nM, 50 nM to 750 nM, 100 nM to 500 nM, 1 nM to 100 nM, 1 nM to 50 nM, 1 nM to 40 nM, 1 nM to 30 nM, 1 nM to 20 nM, most preferably between 1 nM and 10 nM of each of the antisense oligomer (s) of the invention.

The composition may comprise about 1 nM, 2 nM, 3 nM, 4 nM, 5 nM, 6 nM, 7 nM, 8 nM, 9 nM, 10 nM, 20 nM, 50 nM, 75 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM or 1000 nM of each of the desired antisense oligomer(s) of the invention.

The present invention further provides one or more antisense oligomers adapted to aid in the prophylactic or therapeutic treatment, prevention or amelioration of symptoms of a disease such as an OPA1 expression related disease or pathology in a form suitable for delivery to a patient.

The phrase "pharmaceutically acceptable" refers to molecular entities and compositions that are physiologically tolerable and do not typically produce an allergic or similarly untoward reaction, such as gastric upset and the like, when administered to a patient. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Remington: The Science and Practice of Pharmacy, 22nd Ed., Pharmaceutical Press, PA (2013).

In a more specific form of the invention there are provided pharmaceutical compositions comprising therapeutically effective amounts of one or more antisense oligomers of the invention together with pharmaceutically acceptable diluents, preservatives, solubilizers, emulsifiers, adjuvants, and/or carriers. Such compositions include diluents of various buffer content (e.g. Tris-HCl, acetate, phosphate), pH and ionic strength and additives such as detergents and solubilizing agents (e.g. Tween 80, Polysorbate 80), antioxidants (e.g., ascorbic acid, sodium metabisulfite), preservatives (e.g. Thimersol, benzyl alcohol) and bulking substances (e.g., lactose, mannitol). The material may be incorporated into particulate preparations of polymeric compounds such as polylactic acid, polyglycolic acid, etc. or into liposomes. Hyaluronic acid may also be used. Such compositions may influence the physical state, stability, rate of in vivo release, and rate of in vivo clearance of the present proteins and derivatives. See, for example, Remington: The Science and Practice of Pharmacy, 22nd Ed., Pharmaceutical Press, PA (2013). The compositions may be prepared in liquid form, or may be in dried powder, such as a lyophilised form.

It will be appreciated that pharmaceutical compositions provided according to the present invention may be administered by any means known in the art. The pharmaceutical compositions for administration are administered by injection, orally, topically or by the pulmonary or nasal route. For example, the antisense oligomers may be delivered by topical, intravenous, intra-arterial, intraperitoneal, intramuscular or subcutaneous routes of administration. The appropriate route may be determined by one of skill in the art, as appropriate to the condition of the subject under treatment. Preferably, the antisense oligomers are delivered topically to the eye or by intraocular injection or intraocular implant, so that the effects on OPA1 production are spatially limited and are not systemic.

Formulations for topical administration include those in which the oligomers of the disclosure are in admixture with a topical delivery agent such as hydrogels, lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). For topical or other administration, oligomers of the disclosure may be encapsulated within liposomes or may form complexes thereto, in particular to cationic liposomes. Alternatively, oligomers may be complexed to lipids, in particular to cationic lipids. Fatty acids and esters, pharmaceutically acceptable salts thereof, and their uses are further described in U.S. Pat. No. 6,287,860 and/or U.S. patent application Ser. No. 09/315,298 filed on May 20, 1999.

In certain embodiments, the antisense oligomers of the disclosure can be delivered by topical or transdermal methods (e.g., via incorporation of the antisense oligomers into, e.g., emulsions, with such antisense oligomers optionally packaged into liposomes) including delivery to ocular surfaces. Such topical or transdermal and emulsion/liposome-mediated methods of delivery are described for delivery of antisense oligomers in the art, e.g., in U.S. Pat. No. 6,965,025. Preferably the topical delivery is delivery to the eye.

The antisense oligomers described herein may also be delivered via an implantable device. Design of such a device is an art-recognized process, with, e.g., synthetic implant design described in, e.g., U.S. Pat. No. 6,969,400. Preferably the implant is able to be implanted into the eye for sustained delivery of the antisense oligomers.

Compositions and formulations for ocular administration, including ocular injection, topical ocular delivery and ocular implant may include sterile aqueous solutions which may also contain buffers, diluents and other suitable additives such as, but not limited to, penetration enhancers, carrier compounds and other pharmaceutically acceptable carriers or excipients.

The delivery of a therapeutically useful amount of antisense oligomers may be achieved by methods previously published. For example, delivery of the antisense oligomer may be via a composition comprising an admixture of the antisense oligomer and an effective amount of a block copolymer. An example of this method is described in US patent application US20040248833. Other methods of delivery of antisense oligomers to the nucleus are described in Mann C J et al. (2001) Proc, Natl. Acad. Science, 98(1) 42-47, and in Gebski et al. (2003) Human Molecular Genetics, 12(15): 1801-1811. A method for introducing a nucleic acid molecule into a cell by way of an expression vector either as naked DNA or complexed to lipid carriers, is described in U.S. Pat. No. 6,806,084.

Antisense oligomers can be introduced into cells using art-recognized techniques (e.g., transfection, electroporation, fusion, liposomes, colloidal polymeric particles and viral and non-viral vectors as well as other means known in the art). The method of delivery selected will depend at least on the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

It may be desirable to deliver the antisense oligomer in a colloidal dispersion system. Colloidal dispersion systems include macromolecule complexes, nanocapsules, microspheres, beads, and lipid-based systems including oil-in-water emulsions, micelles, mixed micelles, and liposomes or liposome formulations. These colloidal dispersion systems can be used in the manufacture of therapeutic pharmaceutical compositions.

Liposomes are artificial membrane vesicles, which are useful as delivery vehicles in vitro and in vivo. These formulations may have net cationic, anionic, or neutral charge characteristics and have useful characteristics for in vitro, in vivo and ex vivo delivery methods. It has been shown that large unilamellar vesicles can encapsulate a substantial percentage of an aqueous buffer containing large macromolecules. RNA and DNA can be encapsulated within the aqueous interior and be delivered to cells in a biologically active form (Fraley, et al., Trends Biochem. Sci. 6:77, 1981).

In order for a liposome to be an efficient gene transfer vehicle, the following characteristics should be present: (1) encapsulation of the antisense oligomer of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988). The composition of the liposome is usually a combination of phospholipids, particularly high phase-transition-temperature phospholipids, usually in combination with steroids, especially cholesterol. Other phospholipids or other lipids may also be used. The physical characteristics of liposomes depend on pH, ionic strength, and the presence of divalent cations. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

As known in the art, antisense oligomers may be delivered using, for example, methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated by reference in its entirety).

The antisense oligomer may also be combined with other pharmaceutically acceptable carriers or diluents to produce a pharmaceutical composition. Suitable carriers and diluents include isotonic saline solutions, for example phosphate-buffered saline. The composition may be formulated for topical, parenteral, intramuscular, intravenous, subcutaneous, intraocular, oral, or transdermal administration.

The routes of administration described are intended only as a guide since a skilled practitioner will be able to readily determine the optimum route of administration and any dosage for any particular animal and condition.

Multiple approaches for introducing functional new genetic material into cells, both in vitro and in vivo have been attempted (Friedmann (1989) Science, 244:1275-

1280). These approaches include integration of the gene to be expressed into modified retroviruses (Friedmann (1989) supra; Rosenberg (1991) Cancer Research 51(18), suppl.: 5074S-5079S); integration into non-retrovirus vectors (Rosenfeld, et al. (1992) Cell, 68:143-155; Rosenfeld, et al. (1991) Science, 252:431-434); or delivery of a transgene linked to a heterologous promoter-enhancer element via liposomes (Friedmann (1989), supra; Brigham, et al. (1989) Am. J. Med. Sci., 298:278-281; Nabel, et al. (1990) Science, 249:1285-1288; Hazinski, et al. (1991) Am. J. Resp. Cell Molec. Biol., 4:206-209; and Wang and Huang (1987) Proc. Natl. Acad. Sci. (USA), 84:7851-7855); coupled to ligand-specific, cation-based transport systems (Wu and Wu (1988) J. Biol. Chem., 263:14621-14624) or the use of naked DNA, expression vectors (Nabel et al. (1990), supra); Wolff et al. (1990) Science, 247:1465-1468). Direct injection of trans-genes into tissue produces only localized expression (Rosen-feld (1992) supra); Rosenfeld et al. (1991) supra; Brigham et al. (1989) supra; Nabel (1990) supra; and Hazinski et al. (1991) supra). The Brigham et al. group (Am. J. Med. Sci. (1989) 298:278-281 and Clinical Research (1991) 39 (abstract)) have reported in vivo transfection only of lungs of mice following either intravenous or intratracheal administration of a DNA liposome complex. An example of a review article of human gene therapy procedures is: Anderson, Science (1992) 256:808-813; Barteau et al. (2008), Curr Gene Ther; 8(5):313-23; Mueller et al. (2008). Clin Rev Allergy Immunol; 35(3):164-78; Li et al. (2006) Gene Ther., 13(18):1313-9; Simoes et al. (2005) Expert Opin Drug Deliv; 2(2):237-54.

The antisense oligomers of the invention encompass any pharmaceutically acceptable salts, esters, or salts of such esters, or any other compound which, upon administration to an animal including a human, is capable of providing (directly or indirectly) the biologically active metabolite or residue thereof. Accordingly, as an example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention, i.e. salts that retain the desired biological activity of the parent compound and do not impart undesired toxicological effects thereto. For oligomers, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. The pharmaceutical compositions of the present invention may be administered in a number of ways depending upon whether local or systemic treatment is desired and upon the area to be treated. Administration may be via topical (including ophthalmic and mucous membranes, as well as rectal delivery), pulmonary (e.g., by inhalation or insufflation of powders or aerosols, including by nebulizer, intratracheal, intranasal, epidermal and transdermal), oral or parenteral routes. Parenteral administration includes intravenous, intra-arterial, subcutaneous, intraperitoneal, intraocular or intra-muscular injection or infusion; or intracranial, e.g., intrathecal or intraventricular, administration. Oligomers with at least one 2'-O-methoxyethyl modification are believed to be particularly useful for intraocular administration. Preferably, the antisense oligomer is delivered via the intraocular route.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general, the formulations are prepared by uniformly and intimately bringing into association the active ingredients with liquid carriers or finely divided solid carriers or both, and then, if necessary, shaping the product.

Use

According to another aspect of the invention there is provided the use of one or more antisense oligomers as described herein in the manufacture of a medicament for the modulation or control of a disease associated with OPA1 protein expression.

The invention also provides for the use of purified and isolated antisense oligomers as described herein, for the manufacture of a medicament for treatment of a disease associated with OPA1 protein expression.

There is also provided the use of purified and isolated antisense oligomers as described herein, for the manufacture of a medicament to treat, prevent or ameliorate the effects of a disease associated with OPA1 protein expression.

Preferably, the OPA1-related disease is ADOA. Preferably the disease associated with OPA1 protein expression is associated with decreased levels of functional OPA1 protein. Preferably the decreased levels of functional OPA1 protein are in patients who have ADOA, more preferably in ADOA where OPA1 haploinsufficiency is implicated.

The invention extends, according to a still further aspect thereof, to cDNA or cloned copies of the antisense oligomer sequences of the invention, as well as to vectors containing the antisense oligomer sequences of the invention. The invention extends further also to cells containing such sequences and/or vectors.

Kits

There is also provided a kit to treat, prevent or ameliorate the effects of a disease associated with OPA1 protein expression in a patient, which kit comprises at least an antisense oligomer as described herein and combinations or cocktails thereof, packaged in a suitable container, together with instructions for its use. Preferably the disease associated with OPA1 protein expression is ADOA.

In a preferred embodiment, the kits will contain at least one antisense oligomer as described herein or as shown in Table 1, or SEQ ID NOs: 1-60; more preferably SEQ ID NOs: 5, 9, 13, 16-18, 20-27, 30, 32, 42, 49-52, 54-55 and 57; even more preferably SEQ ID NOs: 5, 22, 23, 25, 30 and 57, or a cocktail of antisense oligomers, as described herein. The kits may also contain peripheral reagents such as buffers, stabilizers, etc.

When the components of the kit are provided in one or more liquid solutions, the liquid solution can be an aqueous solution, for example a sterile aqueous solution. For in vivo use, the expression construct may be formulated into a pharmaceutically acceptable syringeable composition. In this case the container means may itself be an inhalant, syringe, pipette, eye dropper, or other such like apparatus, from which the formulation may be applied to an affected area of the animal, such as the lungs, injected into an animal, or even applied to and mixed with the other components of the kit.

In an embodiment, the kit of the present invention comprises a composition comprising a therapeutically effective amount of an antisense oligomer capable of binding to a selected target on an OPA1 gene transcript to modify translation in an OPA1 gene transcript or part thereof. In an alternative embodiment, the formulation is in pre-measured, pre-mixed and/or pre-packaged. Preferably, the intraocular solution is sterile.

The kit of the present invention may also include instructions designed to facilitate user compliance. Instructions, as used herein, refers to any label, insert, etc., and may be positioned on one or more surfaces of the packaging material, or the instructions may be provided on a separate sheet, or any combination thereof. For example, in an embodiment, the kit of the present invention comprises instructions for administering the formulations of the present invention. In one embodiment, the instructions indicate that the formulation of the present invention is suitable for the treatment of ADOA. Such instructions may also include instructions on dosage, as well as instructions for administration via topical delivery to the eye or via intraocular injection.

The antisense oligomers and suitable excipients can be packaged individually so to allow a practitioner or user to formulate the components into a pharmaceutically acceptable composition as needed. Alternatively, the antisense oligomers and suitable excipients can be packaged together, thereby requiring de minimis formulation by the practitioner or user. In any event, the packaging should maintain chemical, physical, and aesthetic integrity of the active ingredients.

General

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg. Size, displacement and field strength etc). A range of values will be understood to include all values within the range, including the values defining the range, and values adjacent to the range which lead to the same or substantially the same outcome as the values immediately adjacent to that value which defines the boundary to the range. Accordingly, unless indicated to the contrary, the numerical parameters set forth in the specification and claims are approximations that may vary depending upon the desired properties sought to be obtained by the present invention. Hence "about 80%" means "about 80%" and also "80%". At the very least, each numerical parameter should be construed in light of the number of significant digits and ordinary rounding approaches.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs. The term "active agent" may mean one active agent or may encompass two or more active agents.

Sequence identity numbers ("SEQ ID NO:") containing nucleotide and amino acid sequence information included in this specification are collected at the end of the description and have been prepared using the program Patent In Version 3.0. Each nucleotide or amino acid sequence is identified in the sequence listing by the numeric indicator <210> followed by the sequence identifier (e.g. <210>1, <210>2, etc.). The length, type of sequence and source organism for each nucleotide or amino acid sequence are indicated by information provided in the numeric indicator fields <211>, <212> and <213>, respectively. Nucleotide and amino acid sequences referred to in the specification are defined by the information provided in numeric indicator field <400> followed by the sequence identifier (e.g. <400>1, <400>2, etc.).

An antisense oligomer nomenclature system was proposed and published to distinguish between the different antisense oligomers (see Mann et al., (2002) J Gen Med 4, 644-654). This nomenclature became especially relevant when testing several slightly different antisense oligomers, all directed at the same target region, as shown below:

H#A/D(x:y)

the first letter designates the species (e.g. H: human, M: murine)

"#" designates target exon number

"A/D" indicates acceptor or donor splice site at the beginning and end of the exon, respectively (x y) represents the annealing coordinates where "−" or "+" indicate intronic or exonic sequences respectively. As an example, A(−6+18) would indicate the last 6 bases of the intron preceding the target exon and the first 18 bases of the target exon. The closest splice site would be the acceptor so these coordinates would be preceded with an "A". Describing annealing coordinates at the donor splice site could be D(+2-18) where the last 2 exonic bases and the first 18 intronic bases correspond to the annealing site of the antisense oligomer. Entirely exonic annealing coordinates that would be represented by A(+65+85), that is the site between the 65th and 85th nucleotide, inclusive, from the start of that exon.

The following examples serve to more fully describe the manner of using the above-described invention, as well as to set forth the best modes contemplated for carrying out various aspects of the invention. It is understood that these methods in no way serve to limit the true scope of this invention, but rather are presented for illustrative purposes.

EXAMPLES

Example 1

Designing ASOs

Figure 1:
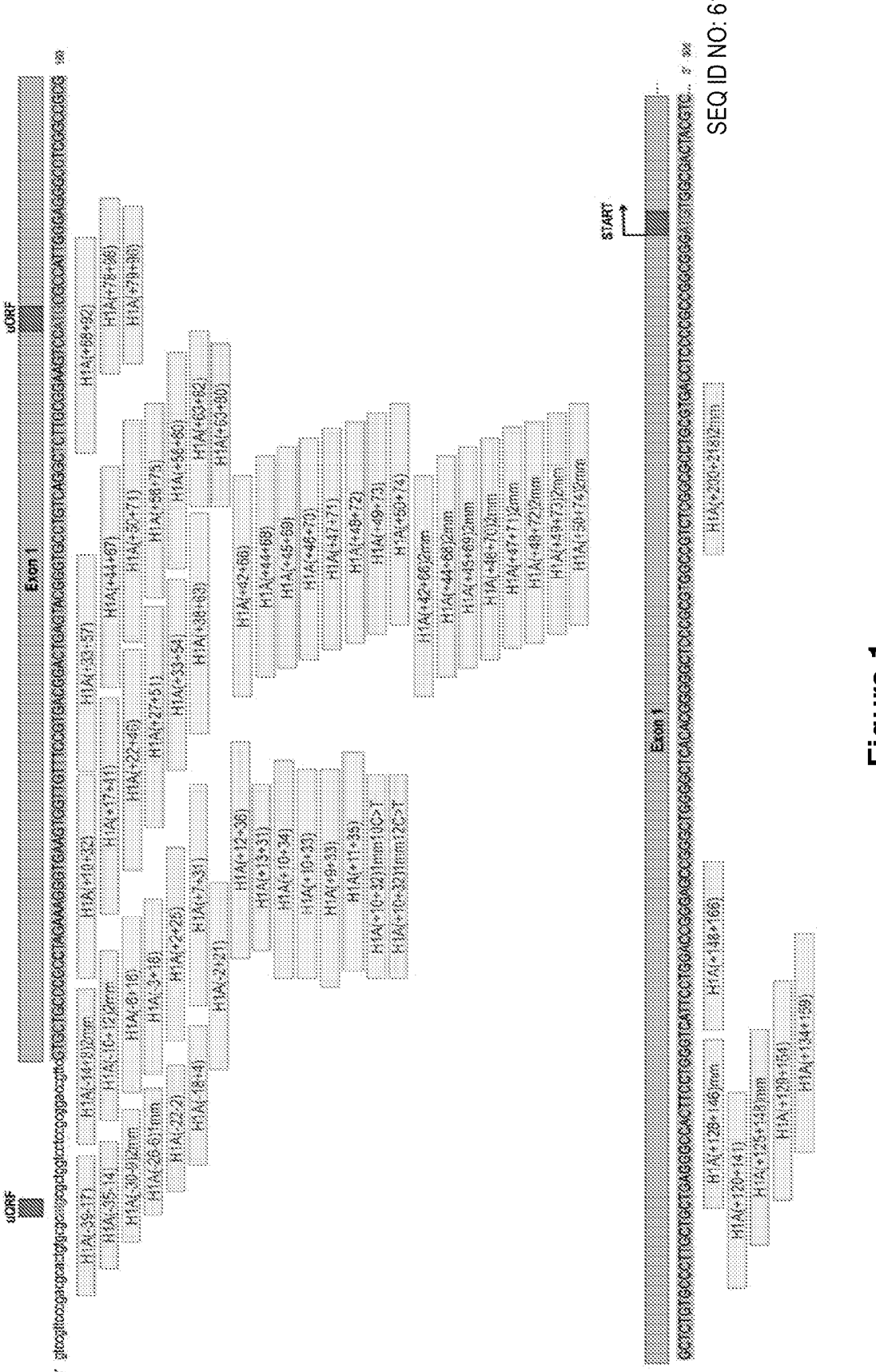
FIG. 1 is a schematic of the antisense oligonucleotides targeting the OPA1 5'UTR and upstream open reading frames (uORFs).

The 5' UTR region of OPA1 is shown in FIG. 1. Antisense oligonucleotides (ASOs) were designed to target the 5' UTR with an aim to sterically inhibit the 5'UTR secondary structure and inhibit selection of the uORF.

Example 2

Figure 2:
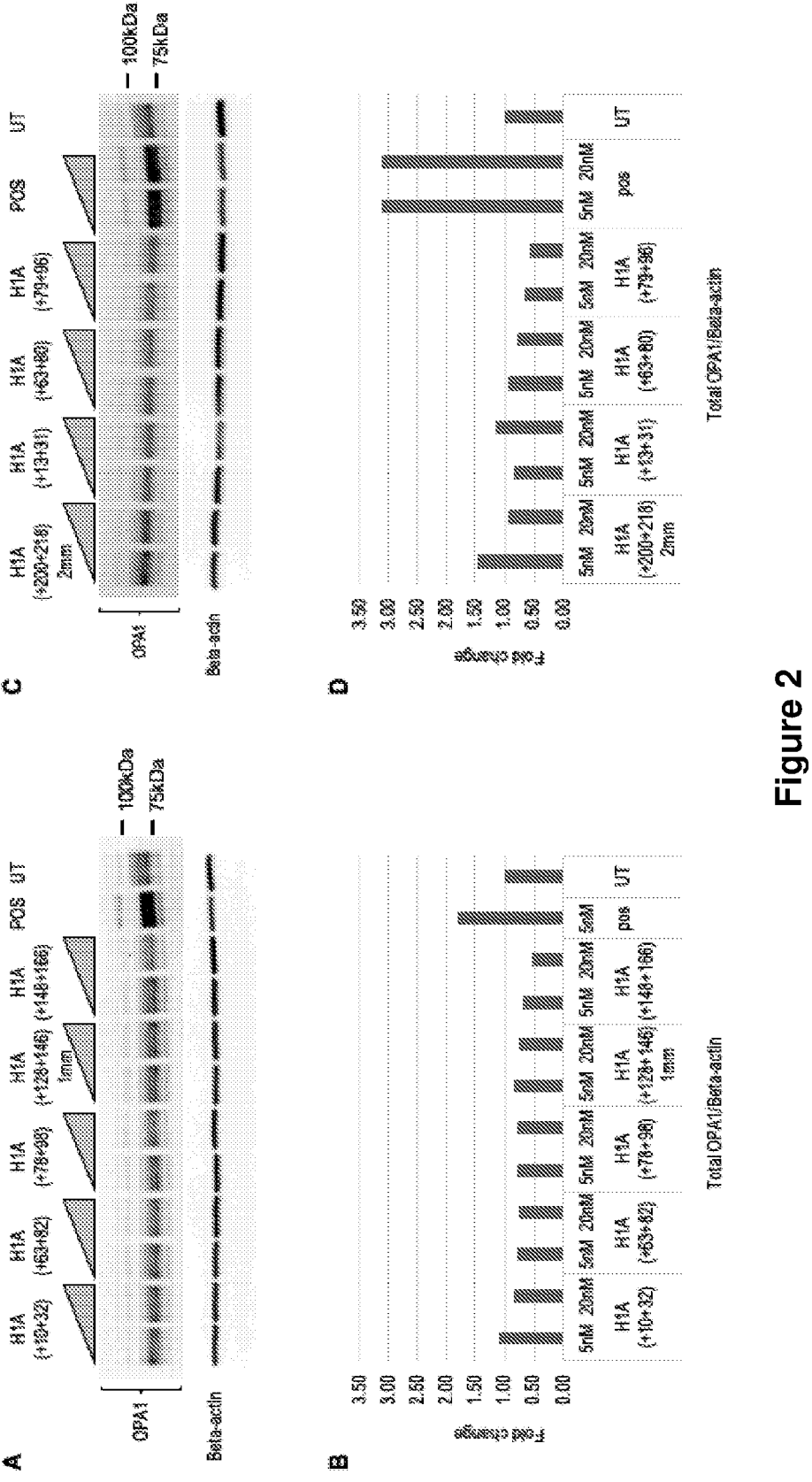
FIG. 2 shows screening of 2'-O-Methoxyethyl-(2'-MOE) ASOs (5 and 20 nM) in HEK293 cells. HEK293 cells were transfected for 48 hrs with 2'-MOE ASOs targeting the OPA1 5'UTR as indicated. A positive control ASO that induces exon 7× skipping was included for comparison. The western blot gel image shows OPA1 protein expression and Beta-actin as a loading control (A, C). The band intensity of OPA1 expression was normalised to Beta-actin (assessed by imageJ™). The OPA1 expression in untreated cells was set to 1 (B, D).

Screening 2'-O-Methoxyethyl (2'MOE) ASOs Targeting the 5'UTR of OPA1 in Human Embryonic Kidney Cells Screening of 2'MOE-ASOs targeting 5'UTR was performed in HEK293 cells using Lipofectamine 2000 (Life Technologies), as per the manufacturer's instruction. Total protein was harvested (48 hr) from the transfected cells using the CytoBuster protein extraction reagent (Merck Millipore) following the manufacturer's instruction and assessed by western blot using rabbit anti-OPA1 monoclonal antibody (Cell Signaling, catalog number 67589) at a dilution of 1:500 in 5% BSA in TBST buffer. The screening 2'MOE-ASOs was transfected in parallel with a positive control ASO. However, no OPA1 upregulation was observed in designed 2'MOE-ASO sequences as compared to the positive control (FIG. 2).

Example 3

Figure 3:
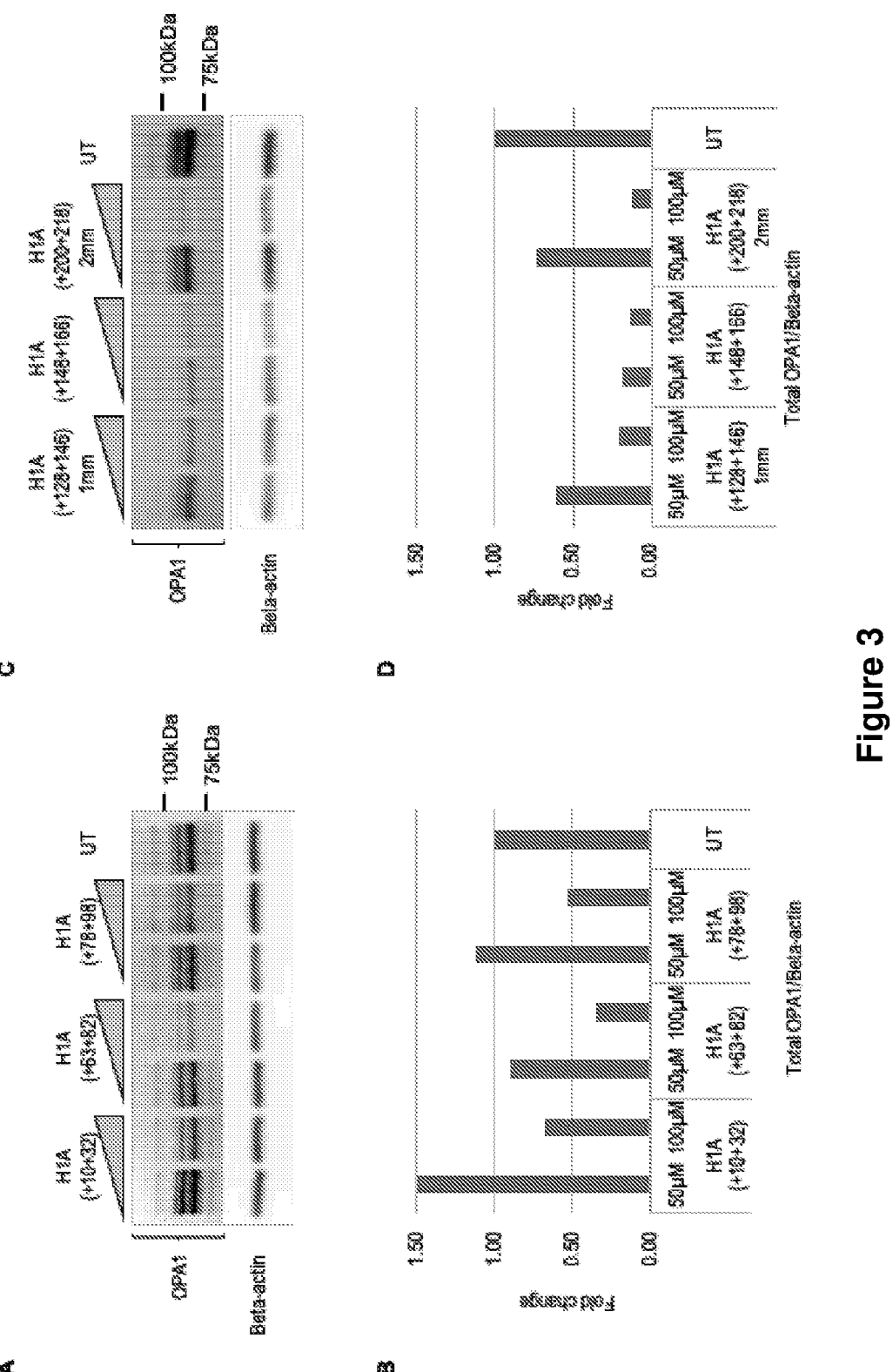
FIG. 3 shows screening of PMOs (50 and 100 μM) in HEK293 cells. HEK293 cells were transfected for 48 hrs with PMOs targeting the OPA1 5'UTR as indicated. The western blot gel image shows OPA1 protein expression and Beta-actin as a loading control (A, C). The band intensity of OPA1 expression was normalised to Beta-actin (assessed by imageJ™) The OPA1 expression in untreated cells was set to 1 (B, D).

Screening Phosphorodiamidate Morpholino Oligomers (PMOs) Targeting the 5'UTR of OPA1 in Human Embryonic Kidney Cells PMOs targeting the 5'UTR of OPA1 were nucleofected into HEK293 cells using NEON® electroporation system (ThermoFisher®). Total protein was harvested with Cyto-Buster protein extraction reagent at 48 hr post-transfection and OPA1 protein levels were determined by western blot assay. The PMO OPA1_H1A(+10+32) induced OPA1 protein expression up to 1.5-fold as compared to untreated HEK293 cell (FIG. 3).

Example 4

Figure 4:
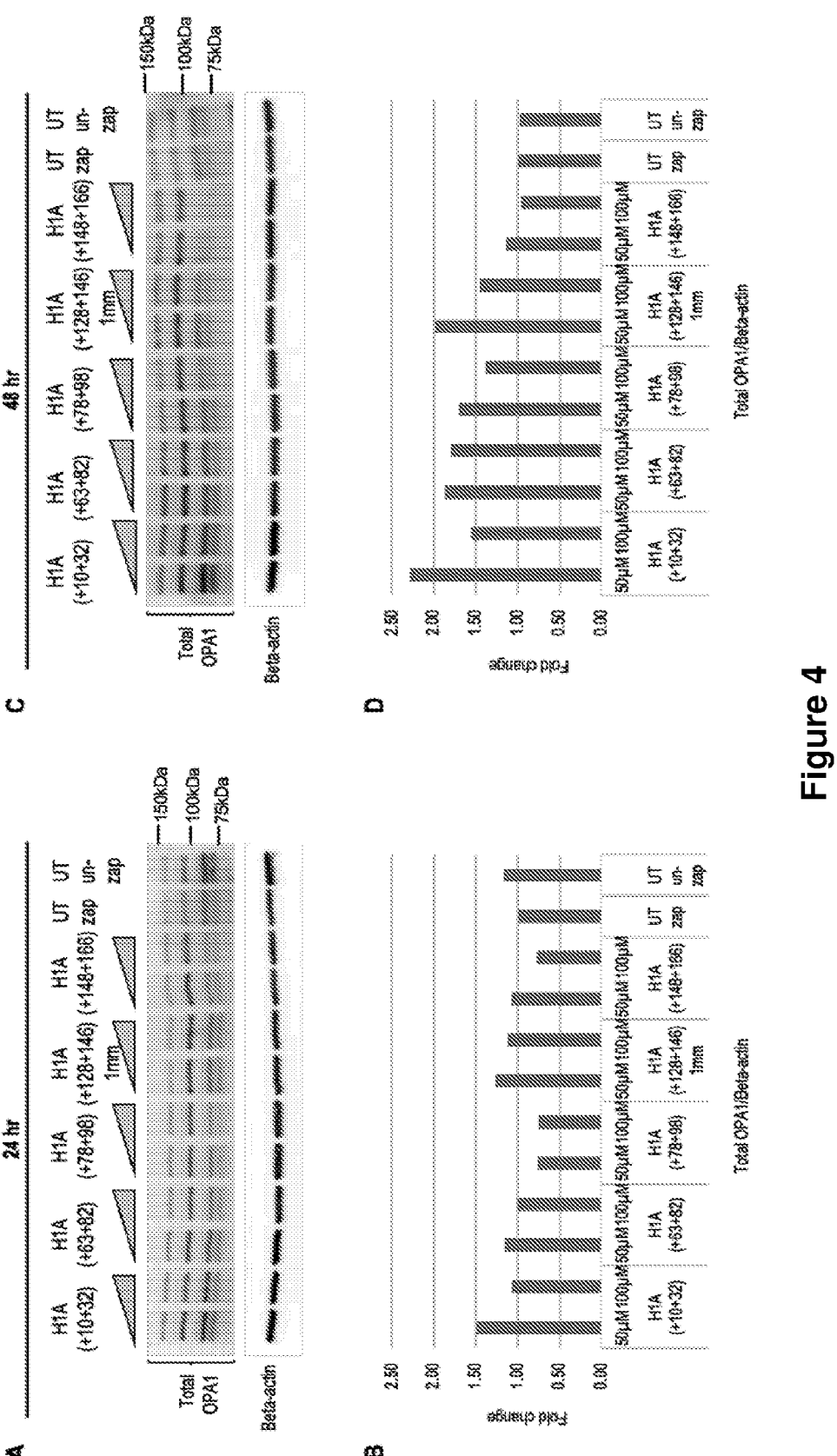
FIG. 4 shows screening of PMOs (50 and 100 μM) in ADOA patient fibroblasts. The western blot gel image shows OPA1 expression in patient fibroblasts transfected with PMOs targeting the OPA1 5' UTR at 24 hr (A) and 48 hr (B).

Screening Phosphorodiamidate Morpholino Oligomers (PMOs) Targeting the 5'UTR of OPA1 in ADOA Patient Fibroblasts PMOs targeting the 5'UTR of OPA1 were transfected into patient fibroblasts carrying the OPA1 mutation (c.2708_2711delTTAG) using NEON® electroporation system. The total protein was collected at 24 hr and 48 hr post-transfection and assessed by Western blot assay. Most of the PMOs upregulated OPA1 protein expression compared to untreated control in a time-dependent manner. The PMO OPA1_H1A(+10+32) showed the highest upregulation of OPA1 protein expression; up to 2-fold at 48 hr as compared to untreated patient fibroblasts (FIG. 4).

Figure 5A:
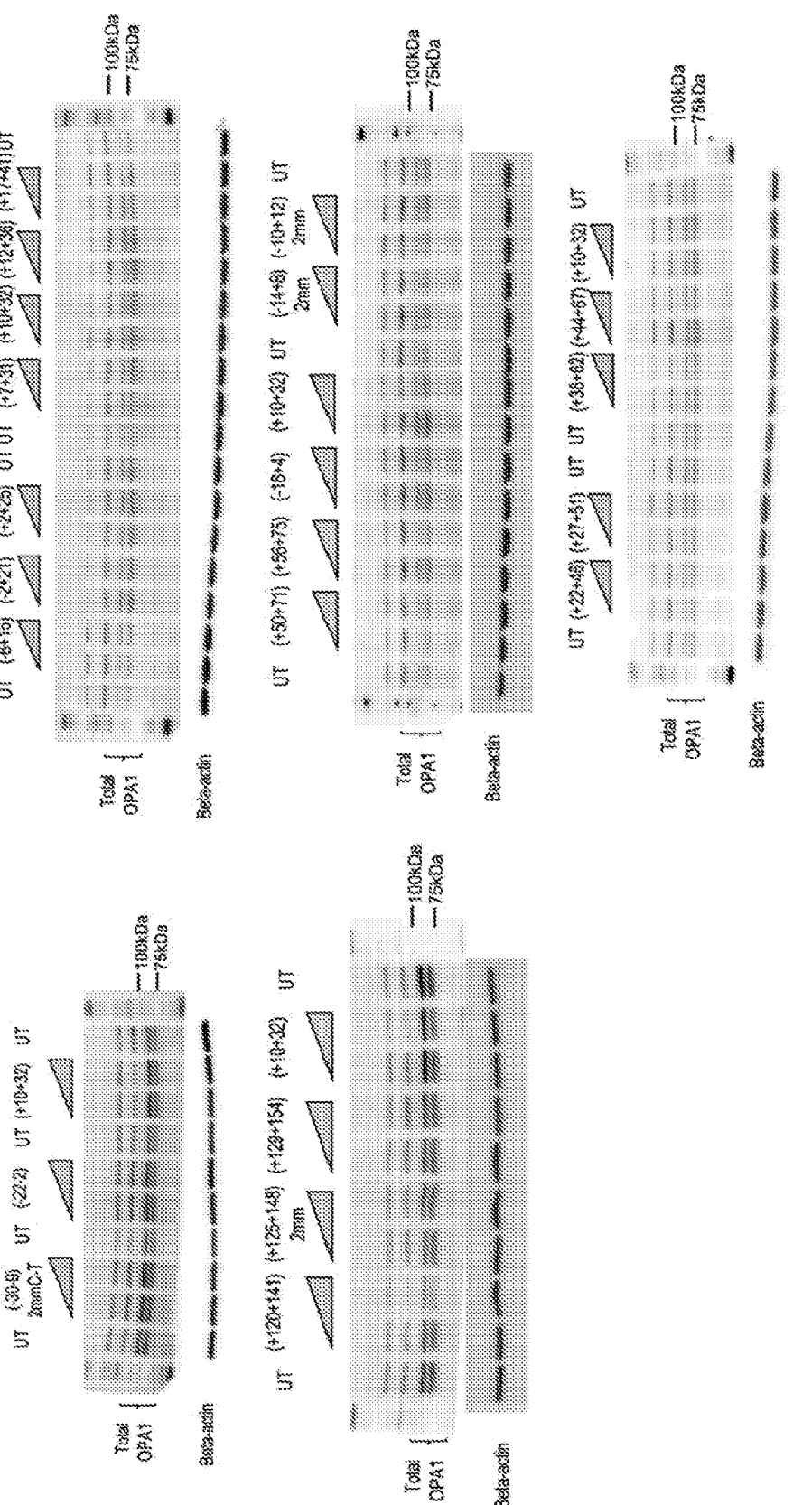
Figure 5B:
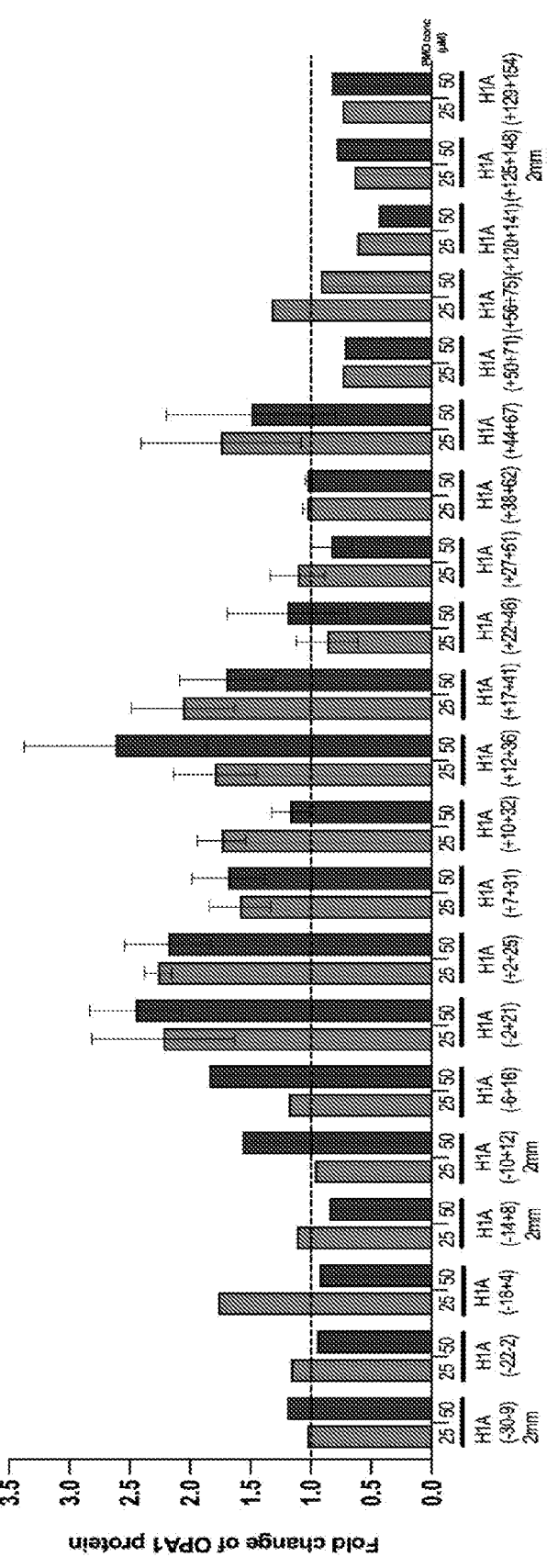

PMOs targeting the 5'UTR of OPA1 were transfected in patient fibroblasts carrying the OPA1 mutation (c.2708_2711delTTAG) using NEON® electroporation system. The total protein was harvested at 48 hr post-transfection and assessed for OPA1 protein expression using western blot assay. PMOs OPA1_H1A(−2+21), H1A(+2+25), H1A (+7+31), H1A(+12+36), H1A(+17+41) and H1A(+44+67) showed higher upregulation of OPA1 protein expression comparison to PMO H1A(+10+32) treated conditions (FIGS. 5A and 5B).

Example 5

Designing Microwalked PMOs

Microwalked PMOs targeting the 5'UTR of OPA1 adjacent to the OPA1_H1A(+10+32) were transfected in patient fibroblasts carrying the OPA1 mutation (c.2708_2711delTTAG) using NEON® electroporation system. Total protein was harvested (48 hr) from the transfected cells using the CytoBuster protein extraction reagent (Merck Millipore) following the manufacturer's instruction and assessed by western blot assay using rabbit anti-OPA1 monoclonal antibody (Cell Signaling, catalogue number 67589) at a dilution of 1:250 in 5% BSA in TBST buffer followed by goat anti-rabbit IgG H&L antibody (abcam, catalogue number ab216773, IRDye® 800CW). Beta-actin was served as loading control and was detected using monoclonal mouse anti-β-actin antibody (Sigma-Aldrich, catalogue number A5441) followed by goat anti-mouse IgG H&L antibody (abcam, catalogue number ab216776, IRDye® 680RD). PMO H1A(+10+32) 1 mm10C>T increased OPA1 expression above that induced by the parental sequence H1A(+10+32) (FIG. 6).

Figure 7A:
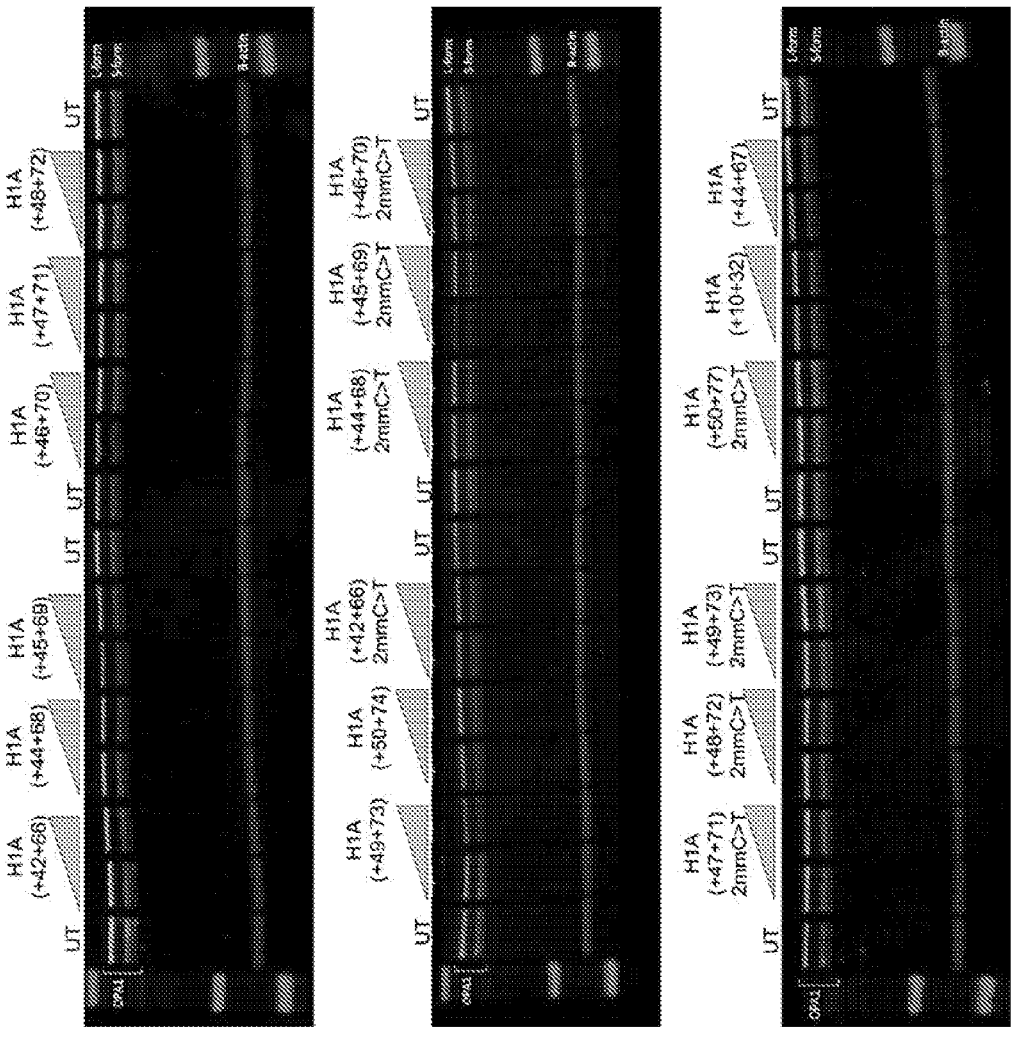
Figure 7B:
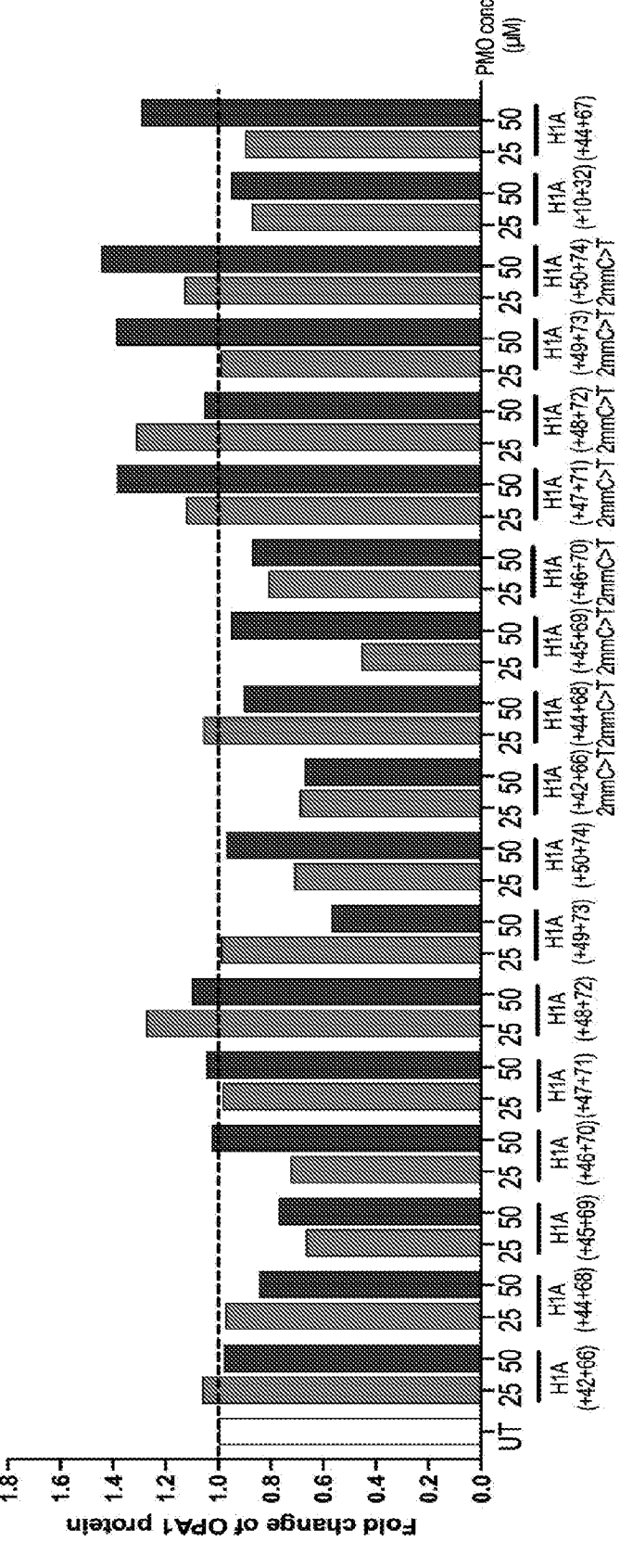

Microwalked PMOs targeting the 5'UTR of OPA1 adjacent to the PMO OPA1_H1A(+44+67) were transfected in patient fibroblasts carrying the OPA1 mutation (c.2708_2711delTTAG) using NEON® electroporation system. Total protein was harvested (48 hr) from the transfected cells using the CytoBuster protein extraction reagent (Merck Millipore) following the manufacturer's instruction and assessed by western blot assay using rabbit anti-OPA1 monoclonal antibody (Cell Signaling, catalogue number 67589) at a dilution of 1:250 in 5% BSA in TBST buffer followed by goat anti-rabbit IgG H&L antibody (abcam, catalogue number ab216773, IRDye® 800CW). Beta-actin was served as loading control and was detected using monoclonal mouse anti-β-actin antibody (Sigma-Aldrich, catalogue number A5441) followed by goat anti-mouse IgG H&L antibody (abcam, catalogue number ab216776, IRDye® 680RD). PMOs H1A(+47+71) 2 mmC>T, H1A(+49+73) 2 mmC>T, and H1A(+50+74) 2 mmC>T increased OPA1 expression above that induced by the parental sequence H1A(+44+67) (FIGS. 7A and 7B).

Example 6

Screening Peptide-Conjugated Phosphorodiamidate Morpholino Oligomers (PPMOs) Targeting the 5'UTR of OPA1 in ADOA Patient Fibroblasts PPMO_H1A(+10+32) was incubated with ADOA patient fibroblasts carrying the OPA1 mutations (c.2708_2711delTTAG, c.985-1G>A and c.2608delA) for 7 days. Cells were harvested for the assessment of OPA1 protein expression using western blot analysis and normalised with beta-actin expression. PPMO_H1A(+10+32) increased OPA1 protein expression in a dose dependent manner (FIG. 8). Improvement in mitochondrial function was evaluated following PPMO_H1A(+10+32) treatment. At day 7 post treatment, PPMO-treated cells were subsequently incubated with 5 mM 2-Deoxy-D-glucose (Sigma, catalogue number D8375) and 5 mM sodium pyruvate (Thermo Fisher, catalogue number 11360-070) for 18 hr and quantified for mitochondrial ATP using the CellTitre-Glo Luminescent Cell Viability Assay (Promega, catalogue number G7572) following the manufacturer's instructions. PPMO_H1A(+10+3 2) increased mitochondrial ATP levels in fibroblasts from 4 ADOA patients (FIG. 9).

Example 7

Screening PPMOs Targeting the 5'UTR of OPA1 in ADOA Patient Fibroblasts

PPMO_H1A(+1 0+3 2) was incubated with patient fibroblasts carrying the OPA1 mutations (c.2708_2711delTTAG and c.985-1G>A) for 7 days and was assessed for protective effects against apoptosis. PPMO-treated cells were treated with 25-50 µM oligomycin for 4 hrs prior to cell harvest. Cells were stained with Annexin V and propidium iodide and analysed for cell apoptosis using flow cytometry. PPMO_H1A(+10+32) protected cells from apoptosis in a dose dependent manner in fibroblasts from 3 ADOA patients (FIG. 10). NT; not tested.

The invention claimed is:

1. An antisense oligomer for increasing mRNA translation of the optic atrophy 1 (OPA1) gene transcript or part thereof which has a modified backbone structure and wherein the antisense oligomer comprises SEQ ID NO: 57.

2. The antisense oligomer of claim 1 wherein the antisense oligomer contains one or more nucleotide positions subject to an alternative chemistry or modification chosen from the list comprising: (i) modified sugar moieties; (ii) resistance to RNase H; and/or (iii) oligomeric mimetic chemistry.

3. The antisense oligomer of claim 1 wherein the antisense oligomer is a phosphorodiamidate morpholino oligomer.

4. The antisense oligomer of claim 1 wherein when any thymine (T) is present in the nucleotide sequence, the thymine (T) may be replaced by a uracil (U).

5. The antisense oligomer of claim 1 that operates to:
   i. hybridise to the 5'UTR of the OPA1 gene transcript and disrupt initiation of aberrant translation of the OPA1 gene transcript or part thereof; and/or
   ii. increase translation of functional OPA1 protein through steric inhibition of 5'UTR secondary structure elements.

6. The antisense oligomer of claim 1 that operates to:
   i. increase mitochondrial ATP levels; and/or
   ii. reduce apoptosis
   in the cells of patients with OPA1 mutations.

7. A pharmaceutical or therapeutic composition, the composition comprising:
   a) one or more antisense oligomers according to claim 1, and
   b) one or more pharmaceutically acceptable carriers and/or diluents.

8. A method to treat ameliorate the effects of a disease associated with optic atrophy 1 (OPA1) expression, comprising the step of:
   a) administering to the patient an effective amount of one or more antisense oligomers according to claim 1.

9. The method of claim 8, wherein the OPA1 expression related disease is Autosomal Dominant Optic Atrophy (ADOA).

10. The method of claim 8, wherein the subject with the disease associated with OPA1 expression is a human.

11. The method of claim 8, that results in between 1.1- and 2.5-fold higher expression of the OPA1 protein than the expression of the OPA1 protein in subjects with symptomatic OPA1 mutations.

* * * * *